(12) United States Patent
Solin et al.

(10) Patent No.: US 8,436,436 B2
(45) Date of Patent: May 7, 2013

(54) MULTIFUNCTIONAL NANOSCOPY FOR IMAGING CELLS

(75) Inventors: Stuart A. Solin, St. Louis, MO (US); Kirk D. Wallace, St. Louis, MO (US); Samuel A. Wickline, St. Louis, MO (US); Michael S. Hughes, Wildwood, MO (US)

(73) Assignee: Washington University, St. Louis, MO (US)

( * ) Notice: Subject to any disclaimer, the term of this patent is extended or adjusted under 35 U.S.C. 154(b) by 680 days.

(21) Appl. No.: 12/375,861

(22) PCT Filed: Jul. 31, 2007

(86) PCT No.: PCT/US2007/074864
§ 371 (c)(1),
(2), (4) Date: May 28, 2009

(87) PCT Pub. No.: WO2008/115258
PCT Pub. Date: Sep. 25, 2008

(65) Prior Publication Data
US 2009/0326337 A1    Dec. 31, 2009

Related U.S. Application Data

(60) Provisional application No. 60/821,040, filed on Aug. 1, 2006.

(51) Int. Cl.
*G01P 15/08* (2006.01)
*A61B 5/00* (2006.01)
*G01B 7/16* (2006.01)

(52) U.S. Cl.
USPC ............................. 257/417; 600/300; 73/777

(58) Field of Classification Search .............. 257/417; 600/300; 73/777; 324/71.1; 435/287.1
See application file for complete search history.

(56) References Cited

U.S. PATENT DOCUMENTS

| | | | |
|---|---|---|---|
| 5,699,215 | A | 12/1997 | Solin et al. |
| 5,965,283 | A | 10/1999 | Solin et al. |

(Continued)

FOREIGN PATENT DOCUMENTS

| | | |
|---|---|---|
| JP | 2005150146 A | 6/2005 |
| JP | 2005227155 A | 8/2005 |

(Continued)

OTHER PUBLICATIONS

A'Amar et al., "Comparison between ultraviolet-visible and near-infrared elastic scattering spectroscopy of chemically induced melanomas in an animal model", Journal of Biomedical Optics, Nov./Dec. 2004, pp. 1320-1326, vol. 9(6).

(Continued)

*Primary Examiner* — William D Coleman
(74) *Attorney, Agent, or Firm* — Thompson Coburn LLP

(57) ABSTRACT

Disclosed herein is an apparatus for sensing characteristics of an object. In a preferred embodiment, the apparatus comprises an array, wherein the array comprises a plurality of nanoscale hybrid semiconductor/metal devices which are in proximity to an object, each hybrid semiconductor/metal device being configured to produce a voltage in response to a perturbation, wherein the produced voltage is indicative of a characteristic of the object. Any of a variety of nanoscale EXX sensors can be selected as the hybrid semiconductor/metal devices in the array. With such an array, ultra high resolution images of nanoscopic resolution can be generated of objects such as living cells, wherein the images are indicative of a variety of cell biologic processes.

119 Claims, 16 Drawing Sheets

U.S. PATENT DOCUMENTS

| | | | |
|---|---|---|---|
| 6,245,601 | B1 | 6/2001 | Kobayashi et al. |
| 6,531,740 | B2 | 3/2003 | Bosco et al. |
| 6,707,122 | B1 | 3/2004 | Hines et al. |
| 6,714,374 | B1 | 3/2004 | Hayashi et al. |
| 6,756,651 | B2 | 6/2004 | Bozso et al. |
| 6,806,508 | B2 | 10/2004 | D'Evelyn et al. |
| 6,881,979 | B2 | 4/2005 | Starikov et al. |
| 6,933,503 | B2 | 8/2005 | Sipila et al. |
| 7,052,588 | B2 | 5/2006 | Gu et al. |
| 7,082,838 | B2 | 8/2006 | Rowe et al. |
| 7,192,873 | B1 | 3/2007 | Kim et al. |
| 7,223,960 | B2 | 5/2007 | Mouli |
| 2002/0084429 | A1 | 7/2002 | Craighead et al. |
| 2002/0129087 | A1 | 9/2002 | Cachin et al. |
| 2002/0192653 | A1 | 12/2002 | Stetter et al. |
| 2004/0008453 | A1 | 1/2004 | Nie |
| 2004/0129069 | A1 | 7/2004 | Rowes et al. |
| 2004/0129087 | A1 | 7/2004 | Rowe et al. |
| 2005/0199731 | A9 | 9/2005 | Empedocles et al. |
| 2006/0036194 | A1 | 2/2006 | Schultheiss et al. |
| 2006/0228723 | A1 | 10/2006 | Bradley et al. |
| 2009/0026082 | A1 | 1/2009 | Rothberg et al. |
| 2009/0152664 | A1 | 6/2009 | Klem et al. |
| 2011/0233382 | A1 | 9/2011 | Solin et al. |

FOREIGN PATENT DOCUMENTS

| | | |
|---|---|---|
| WO | 98/12554 A1 | 3/1998 |
| WO | 01/41214 A1 | 6/2001 |
| WO | 02/25749 A2 | 3/2002 |
| WO | 2004036217 A | 4/2004 |
| WO | 2008/115258 A2 | 9/2008 |
| WO | 2011/085220 A2 | 7/2011 |

OTHER PUBLICATIONS

Abnet et al., "Zinc Concentration in Esophageal Biopsy Specimens Measured by X-Ray Fluorescence and Esophageal Cancer Risk", Journal of National Cancer Institute, Feb. 2005, pp. 301-306, vol. 97, No. 4.

Agasoster et al., "The Interaction of Peripheral Proteins and Membranes Studied with a-Lactalbumin and Phospholipid Bilayers of Various Compositions", Journal of Biological Chemistry, Jun. 2003, pp. 21790-21797, vol. 278, No. 24.

Andersen et al., "A new method to correlate histology with biomechanical properties in urethral tissue. An in-vitro study using light microscopy and scanning acoustic microscopy", APMIS Supplement, 2003, pp. 35-38, vol. 109.

Anderson et al. "Mechanism of Binding and Internalization of ICAM-1-Derived Cyclic Peptides by LFA-1 on the Surface of T Cells: A Potential Method for Targeted Drug Delivery", Pharmaceutical Research, Oct. 2003, pp. 1523-1532, vol. 20.

Anderson et al., "Fluorescence spectroscopy accurately detects irreversible cell damage during hepatic radiofrequency ablation", Surgery, 2004, pp. 524-531, vol. 136, No. 3.

Arnberg et al., "Adenovirus Type 37 Binds to Cell Surface Sialic Acid Through a Charge-Dependent Interaction", Virology, 2002, pp. 33-43, vol. 302.

Baker et al., "The Mathematical Theory of Huygens' Principle", Nature, Apr. 1940, pp. 531-532, vol. 145.

Barr et al., "Scanning Acoustic Microscopy of Neoplastic and Inflammatory Cutaneous Tissue Specimens", The Journal of Investigative Dermatology, Jan. 1991, pp. 38-42, vol. 96, No. 1.

Bayer et al., "Structural Analysis of the Mitotic Regulator hPin1 in Solution—Insights into domain architecture and substrate binding", Journal of Biological Chemistry, Jul. 2003, pp. 26183-26193, vol. 278, No. 28.

Belyaeva et al., "Laser Fluorescence Specroscopy with 5-Aminolevulinic Acid in Operative Gynecology", Laser Physics, 2004, pp. 1207-1213, vol. 14, No. 9.

Bereiter-Hahn et al., "Mechanical basis of cell shape: investigations with the scanning acoustic microscope", Biochemistry Cell Biology, 1995, pp. 337-348, vol. 73.

Bereiter-Hahn, "Architecture of Tissue Cells. The Structural Basis Which Determines Shape and Locomotion of Cells", Acta Biotheoretica, 1985, pp. 139-148, vol. 34.

Bereiter-Hahn, "Scanning acoustic microscopy visualizes cytomechanical responses to cytochalasin D", Journal of Microscopy-Oxford, Apr. 1987, pp. 29-39, vol. 146.

Bigio et al., "Spectroscopic Sensing of Cancer and Cancer Therapy—Current Status of Translational Research", Cancer Biology & Therapy, Mar. 2004, pp. 259-267, vol. 3:3.

Bocsi et al., "Scanning Fluorescent Microscopy Analysis Is Applicable for Absolute and Relative Cell Frequency Determinations", Cytometry, 2004, pp. 1-8, vol. 61A.

Boone et al., "Bone attachment to hydroxyapatite coated polymers", Journal of Biomedical Materials Research, 1989, pp. 183-199, vol. 23.

Bornhop et al., "Luminescent Lanthanide Chelate Contrast Agents and Detection of Lesions in the Hamster Oral Cancer Model", Applied Spectroscopy, 2003, pp. 1216-1222, vol. 57, No. 10.

Breslin et al., "Autofluorescence and Diffuse Reflectance Properties of Malignant and Benigh Breast Tissues", Annals of Surgical Oncology, 2003, pp. 65-70, vol. 11, No. 1.

Brewer et al., "Imaging of the Ovary", Technology in Cancer Research & Treatment, Dec. 2004, pp. 617-627, vol. 3, No. 6.

Brewer et al., "Prevention of Ovarian Cancer: Intraepithelial Neoplasia", Clinical Cancer Research, Jan. 2003, pp. 20-30, vol. 9.

Briggs et al., "Quantitative acoustic microscopy of individual living human cells", Journal of Microscopy, Oct. 1993, pp. 3-12, vol. 172.

Bumrerraj et al., "Scanning Acoustic Microscopy Study of Human Cortical and Trabecular Bone", Annals of Biomedical Engineering, 2001, pp. 1034-1042, vol. 29.

Buttemere et al., "In vivo assessment of thermal damage in the liver using optical spectroscopy", Journal of Biomedical Optics, Sep./Oct. 2004, pp. 1018-1027, vol. 9, No. 5.

Carrasco et al., "Design of a Composite Ethidium—Netropsin—Anilinoacridine Molecule for DNA Recognition", Chembiochem, 2003, pp. 50-61, vol. 4.

Celentano et al., "Preliminary Tests of a Prototype System for Optical and Radionuclide Imaging in Small Animals", IEEE Transactions on Nuclear Science, Oct. 2003, pp. 1693-1701, vol. 50, No. 5.

Chandraratna et al., "Visualization of myocardial cellular architecture using acoustic microscopy", American Heart Journal, Nov. 1992, pp. 1358-1364, vol. 124, No. 5.

Chandrasekharan et al., "Non-resonant Multiphoton Photoacoustic Spectroscopy for Noninvasive Subsurface Chemical Diagnostics", Applied Spectroscopy, 2004, pp. 1325-1333, vol. 58, No. 11.

Chang et al., "Analytical model to describe fluorescence spectra of normal and preneoplastic epithelial tissue: comparison with Monte Carlo simulations and clinical measurements", Journal of Biomedical Optics, May/Jun. 2004, pp. 511-522, vol. 9, No. 3.

Chawla et al., "Biodegradable poly(e-caprolactone) nanoparticles for tumor-targeted delivery of tamoxifen", International Journal of Pharmaceutics, 2002, pp. 127-138, vol. 249.

Chen et al., "Auto-fluorescence spectra of oral submucous fibrosis", Journal of Oral Pathology & Medicine, 2003, pp. 337-343, vol. 32.

Chen, "Introduction to Scanning Tunneling Microscopy", Second Edition, 2008, pp. 23-40, Oxford University Press.

Ciarlet et al., "Differential Infection of Polarized Epithelial Cell Lines by Sialic Acid-Dependent and Sialic Acid-lndependenct Rotavirus Strains", Journal of Virology, Dec. 2001, pp. 11834-11850, vol. 75, No. 23.

Clark et al., "Detection and diagnosis of oral neoplasia with an optical coherence microscope", Journal of Biomedical Optics, Nov./Dec. 2004, pp. 1271-1280, vol. 9, No. 6.

Collier et al., "Determination of Epithelial Tissue Scattering Coefficient Using Confocal Microscopy", IEEE Journal of Selected Topics in Quantum Electronics, Mar./Apr. 2003, pp. 307-313, vol. 9, No. 2.

Crowder et al., "First Experience With Noncavitational Ultrasound Enhancement of Selective Cellular Delivery of Liquid Perfluorocarbon Nanoparticles to Angiogenic Sites", Journal of the American College of Cardiology, Mar. 2003, p. 59A, vol. 41.

Cunderlikova et al., "Electrostatic Properties of Cells Estimated by Absorption and Fluorescence Spectroscopy", Cell Biochemistry and Biophysics, 2004, pp. 1-10, vol. 41.

De Alberquerque et al., "Differential Expression of Sialic Acid and N-acetylgalactosamine Residues on the Cell Surface of Intestinal Epithelial Cells According to Normal or Metastatic Potential", Journal of Histochemistry & Cytochemistry, 2004, pp. 629-640, vol. 52, No. 5.

De Veld et al., "Autofluorescence Characteristics of Healthy Oral Mucosa at Different Anatomical Sites", Lasers in Surgery and Medicine, 2003, pp. 367-376, vol. 32.

Drezek et al., "Optical Imaging of the Cervix", Cancer, Nov. 2003, pp. 2015-2027, vol. 98, No. 9.

Eckardt et al., "Quantitative Measurements of the Mechanical Properties of Human Bone Tissues by Scanning Acoustic Microscopy", Annals of Biomedical Engineering, 2001, pp. 1043-1047, vol. 29.

Errington et al., "Advanced microscopy solutions for monitoring the kinetics and dynamics of drug-DNA targeting in living cells", Advanced Drug Delivery Reviews, 2005, pp. 153-167, vol. 57.

Extended European Search Report for EP Application No. 07874412.5 dated Mar. 2, 2010.

Extended European Search Report for EP Application No. 09010537.0 dated Apr. 8, 2010.

Fantin et al., "A novel mitochondriotoxic small molecule that selectively inhibits tumor cell growth", Cancer Cell, Jul. 2002, pp. 29-42, vol. 2.

Farokhzad et al., "Nanoparticle-Aptamer Bioconjugates: A New Approach for Targeting Prostate Cancer Cells", Cancer Research, Nov. 2004, pp. 7668-7672, vol. 64.

Fasolini et al., "Hot Spots in Tcf4 for the Interaction with b-Catenin", The Journal of Biological Chemistry, Jun. 2003, pp. 21092-21098, vol. 278, No. 23.

Feingold et al., "Enhancement by Retinoic Acid of the Sensitivity of Different Tumor Cell Lines to the Sialic Acid-Specific Toxin of Entamoeba Histolytica", Cancer Letters, 1984, pp. 263-271, vol. 24.

Feng et al., "Nanoparticles of Biodegradable Polymers for Clinical Administration of Paclitaxel", Current Medicinal Chemistry, 2004, pp. 413-424, vol. 11.

Frazier et al., "Synthetic Aperture Techniques with a Virtual Source Element", IEEE Transactions on Ultrasonics, Ferroelectrics, and Frequency Control, Jan. 1998, pp. 196-207, vol. 45, No. 1.

Saijo et al., "Evaluation of the Inner-Surface Morphology of an Artificial Heart by Acoustic Microscopy", Artificial Organs, 2000, pp. 64-69, vol. 24, No. 1.

Saijo et al., "Ultrasonic tissue characterization of collagen in lipid-rich plaques in apoE-deficient mice", Atherosclerosis, 2001, pp. 289-295, vol. 158.

Saijo et al., "Ultrasonic Tissue Characterization of Infarcted Myocardium by Scanning Acoustic Microscopy", Ultrasound in Medicine & Biology, 1997, pp. 77-85, vol. 23, No. 1.

Saijo et al., "Visualization of human umbilical vein endothelial cells by acoustic microscopy", Ultrasonics, 2000, pp. 396-399, vol. 38.

Sasaki et al., "Influence of Tissue Preparation on the Acoustic Properties of Tissue Sections at High Frequencies", Ultrasound in Medicine & Biology, 2003, pp. 1367-1372, vol. 29, No. 9.

Schenk, "Acoustic Microscopy of Red Blood Cells" The Journal of Histochemistry and Cytochemistry, 1988, pp. 1341-1351, vol. 36, No. 10.

Seidler et al., "Dynamical Current Redistribution and Non-Gaussian 1/f Noise", Physical Review Letters, Apr. 1996, pp. 3049-3052, vol. 76, No. 17.

Seidler et al., "Non-Gaussian 1/f noise: Experimental optimization and separation of high-order amplitude and phase correlations", Physical Review B, Apr. 1996, pp. 9753-9759, vol. 53, No. 15.

Sennoune et al., "Vacuolar H+-ATPase in human breast cancer cells with distinct metastatic potential: distribution and functional activity", American Journal of Physiology—Cell Physiology, 2004, pp. C1443-C1452, vol. 286.

Shalaby et al., "Development of novel substrates for tumor immunotherapy", Journal of Controlled Release, 2003, pp. 209-224, vol. 91.

Sherman, "Integral-Transform Formulation of Diffraction Theory", Journal of the Optical Society of America, Dec. 1967, pp. 1490-1498, vol. 57, No. 12.

Shewell et al., "Inverse Diffraction and a New Reciprocity Theorem", Journal of the Optical Society of America, Dec. 1968, pp. 1596-1603, vol. 58, No. 12.

Skala et al., "Investigation of Fiber-Optic Probe Designs for Optical Spectroscopic Diagnosis of Epithelial Pre-Cancers", Lasers in Surgery and Medicine, 2004, pp. 25-38, vol. 34.

Sokolov et al., "Polarized Reflectance Spectroscopy for Pre-Cancer Detection", Technology in Cancer Research & Treatment, Feb. 2004, pp. 1-14, vol. 3, No. 1.

Solin et al., "Enhanced Room-Temperature Geometric Magnetoresistance in Inhomogeneous Narrow-Gap Semiconductors", Science, Sep. 2000, pp. 1530-1532, vol. 289.

Solin et al., "Nonmagnetic Semiconductors as Read-Head Sensors for Ultra-High-Density Magnetic Recording", Applied Physics Letters, 2002, pp. 4012-4014, vol. 80, No. 21.

Solin et al., "Room Temperature Extraordinary Magnetoresistance of Nonmagnetic Narrow-Gap Semiconductor/Metal Composites: Application to Read-Head Sensors for Ultrahigh-Density Magnetic Recording", IEEE Transactions on Magnetics, 2002, pp. 89-94, vol. 38, No. 1.

Solin et al., "Self-Biasing Nonmagnetic Giant Magnetoresistance Sensor", Applied Physics Letters, 1996, pp. 4105-4107, vol. 69.

Spechler, "Review article: what I do now to manage adenocarcinoma risk, and what I may be doing in 10 years' time", Alimentary Pharmacology & Therapeutics, 2004, pp. 105-110, vol. 20.

Stiborova et al., "Monitoring of DNA Adducts in Humans and 32P-Postlabeling Methods. A Review.", Collection of Czechoslovak Chemical Communications, 2004, pp. 476-498, vol. 69.

Suzuki et al., "Paclitaxel Prevents Loss of Pulmonary Endothelial Barrier Integrity During Cold Preservation", Transplantation, Aug. 2004, pp. 524-529, vol. 78, No. 4.

Svistun et al., "Vision Enhancement System for Detection of Oral Cavity Neoplasia Based on Autofluorescence", Head and Neck—Journal for the Sciences and Specialities of the Head and Neck, Mar. 2004, pp. 205-215, vol. 26.

Szachowicz-Petelska et al., "Changes in physico-chemical properties of human large intestine tumour cells membrane", Molecular and Cellular Biochemistry, 2002, pp. 41-47, vol. 238.

Thethi et al., "Decreased Cell Surface Charge in Cystic Fibrosis Epithelia", Cell Biochemistry and Function, 1997, pp. 35-38, vol. 15.

Tomeckova et al., "Comparison of effect of selected synthetic chalcone analogues on mitochondrial outer membrane determined by fluorescence spectroscopy", Journal of Biochemical and Biophysical Methods, 2004, pp. 135-141, vol. 61.

Trynda-Lemiesz, "Human serum albumin: spectroscopic studies of the paclitaxel binding and proximity relationships with cisplatin and adriamycin", Journal of Inorganic Biochemistry, 2004, pp. 1851-1856, vol. 98.

Tunnell et al., "Instrumentation for Multi-modal Spectroscopic Diagnosis of Epithelial Dysplasia", Technology in Cancer Research & Treatment, 2003, pp. 505-514, vol. 2, No. 6.

Vesely et al., "Subtraction Scanning Acoustic Microscopy Reveals Motility Domains in Cells In Vitro", Cell Motility and the Cytoskeleton, 1994, pp. 231-240, vol. 29.

Vigano et al., "Structure, Orientation, and Conformational Changes in Transmembrane Domains of Multidrug Transporters", Accounts of Chemical Research, 2005, pp. 117-126, vol. 38.

Wolf et al., "Comparison of the Kirchhoff and the Rayleigh-Sommerfeld Theories of Diffraction at an Aperture", Journal of the Optical Society of America, May 1964, pp. 587-594, vol. 54, No. 5.

Wright et al., "Use of visual screening methods for cervical cancer screening", Obstetrics and Gynecology Clinics of North America, 2002, pp. 701-734, vol. 29.

Xu et al., "Surface charge and hydrophobicity determine ErbB2 binding to the Hsp90 chaperone complex", Nature Structural & Molecular Biology, Feb. 2005, pp. 120-126, vol. 12, No. 2.

Xu et al., "The Effect of Asymmetric Surface Potentials on the Intramembrane Electric Field Measured with Voltage-Sensitive Dyes", Biophysical Journal, Apr. 2003, pp. 2768-2780, vol. 84.

Ylitalo et al., "Ultrasound Synthetic Aperture Imaging: Monostatic Approach", IEEE Transaction on Ultrasonics, Ferroelectrics, and Frequency Control, May 1994, pp. 333-339, vol. 41, No. 3.

Zawadzki, "Electron transport phenomena in small-gap semiconductors", Advances in Physics, 1974, pp. 435-522, vol. 23.

Zheng et al., Effects of ascorbic acid and sodium selenite on growth and redifferentiation in human hepatoma cells and its mechanisms, Pharmazie, 2002, pp. 265-269, vol. 57.
Zhou et al., "Extraordinary Magnetoresistance in Externally Shunted van der Pauw Plates", Applied Physics Letters, 2001, pp. 667-669, vol. 78, No. 5.
Zoller et al., "Cellular motility in vitro as revealed by scanning acoustic microscopy depends on cell-cell contacts", Cell & Tissue Research, 1997, pp. 43-50, vol. 290.
Branford et al., "Geometric Manipulation of the High-Field Linear Magnetoresistance in InSb Epilayers on GaAs (001)", Applied Physics Letters, 2005, pp. 202116/1-202116/3, vol. 86.
Miller, "An Acoustic Transducer Array for Medical Imaging—Part II", Hewlett-Packard Journal, Oct. 1983, pp. 22-26.
Newaz et al., "A nanoscale Ti/GaAs metal-semiconductor hybrid sensor for room temperature light detection", Applied Physics Letters, 2010, pp. 082105/1-082105/3, vol. 97.
Pashkin et al., "Room-Temperature A1 Single-Electron Transistor Made by Electron-Beam Lithography", Applied Physics Letters, 2000, pp. 2256-2258, vol. 76.
Sze, "Physics of Semiconductor Devices", Second Edition, 1981, pp. 793-795, Wiley-Interscience, New York.
Gammelmark et al., "Multielement Synthetic Transmit Aperture Imaging Using Temporal Encoding", IEEE Transactions on Medical Imaging, Apr. 2003, pp. 552-563, vol. 22, No. 4.
Giraev et al., "Fluorescent-Spectroscopic Research of in Vivo Tissues Pathological Conditions", International Journal of Modern Physics, 2004, pp. 899-910, vol. 18.
Grattarola et al., "Cell adhesion to silicon substrata: characterization by means of optical and acoustic cytometric techniques", Biomaterials, Jan. 1988, pp. 101-106, vol. 9.
Gupta et al., "Cellular uptake, localization and photodynamic effects of haematoporphyrin derivative in human glioma and squamous carcinoma cell lines", Journal of Photochemistry and Photobiology B: Biology, 2003, pp. 107-120, vol. 69.
Hafsteinsson et al., "Acoustic Microscopy—Principles and Applications in the Studies of Biomaterial Microstructure", Scanning Electron Microscopy, 1984, pp. 1237-1247, Part 3.
Hage et al., "Using the laser-induced fluorescence spectroscopy in the differentiation between normal and neoplastic human breast tissue", Lasers in Medical Science, 2003, pp. 171-176, vol. 18.
Hamblin et al., "Effect of Charge on the Interaction of Site-specific Photoimmunoconjugates with Human Ovarian Cancer Cells", Cancer Research, Nov. 1996, pp. 5205-5210, vol. 56.
He et al., "Electrostatic Modulation in Steroid Receptor Recruitment of LXXLL and FXXLF Motifs", Molecular and Cellular Biology, Mar. 2003, pp. 2135-2150, vol. 23, No. 6.
Hein et al., "A comparative study of the application of scanning acoustic microscopy and confocal laser scanning microscopy to the structural assessment of human bones", Annals of Anatomy, 1995, pp. 427-430, vol. 177.
Heiserman et al., "Acoustic Microscopy in Biophysics", Advances in Biological and Medical Physics, 1980, pp. 325-364, vol. 17.
Hildebrand et al., "Acoustic microscopy of living cells", Proceedings of the National Acedemy of Sciences of the United States of America, Mar. 1981, pp. 1656-1660, vol. 78, No. 3.
Hitomi et al., "A New Approach for Glomerular Lesions: Evaluation of Scanning Acoustic Microscopy (SAM) for Experimental Glomerular Disease in Rats", Ultrasound in Medicine & Biology, 2000, pp. 571-577, vol. 26, No. 4.
Hsu et al., "A Far-red Fluorescent Contrast Agent to Image Epidermal Growth Factor Receptor Expression", Photochemistry and Photobiology, 2004, pp. 272-279, vol. 79, No. 3.
Huang et al., "Laser-induced autofluorescence microscopy of normal and tumor human colonic tissue", International Journal of Oncology, 2004, pp. 59-63, vol. 24.
Hug et al., "Effect of Diethylaminoethyl-dextran on Colony Formation of Human Tumor Cells in Semisolid Suspension Cultures", Cancer Research, Jan. 1983, pp. 210-213, vol. 43.
Hughes, "Analysis of digitized waveforms using Shannon entropy", Journal of the Acoustical Society of America, Feb. 1993, pp. 892-906, vol. 93, No. 2.
Hughes, "Analysis of digitized waveforms using Shannon entropy. II. High-speed algorithms based on Green's functions", Journal of the Acoustical Society of America, May 1994, pp. 2582-2588, vol. 95(5).
Hughes, "Analysis of Ultrasonic Waveforms Using Shannon Entropy", IEEE Ultrasonics Symposium, 1992, pp. 1205-1209.
International Preliminary Report on Patentability (Chapter I) for PCT/US2007/074864 dated Apr. 9, 2009.
International Search Report and Written Opinion for PCT/US2007/074864 dated Jul. 25, 2008.
Israel et al., "Cell wall appositions and plant disease resistance: Acoustic microscopy of papillae that block fungal ingress", Proceedings of the National Academy of Sciences of the United States of America, Apr. 1980, pp. 2046-2049, vol. 77, No. 4.
Jankowiak et al., "Role of Fluorescence Line-Narrowing Spectroscopy and Related Luminescence-Based Techniques in the Elucidation of Mechanisms of Tumor Initiation by Polycyclic Aromatic Hydrocarbons and Estrogens", Journal of Physical Chemistry B, 2004, pp. 10266-10283, vol. 108.
Johnston et al., "Acoustic microscopy: Resolution of subcellular detail", Proceedings of the National Academy of Science of the United States of America, Jul. 1979, pp. 3325-3329, vol. 76, No. 7.
Jorgensen et al., "Small Intestine Wall Distribution of Elastic Stiffness Measured With 500 MHz Scanning Acoustic Microscopy", Annals of Biomedical Engineering, 2001, pp. 1059-1063, vol. 29.
Kallinteri et al., "Arsenic Trioxide Liposomes: Encapsulation Efficiency and in Vitro Stability", Journal of Liposome Research, 2004, pp. 27-38, vol. 14, Nos. 1 & 2.
Kameyama et al., "Evaluation of elastic structural change in coronary atherosclerosis using scanning acoustic microscopy", Atherosclerosis, 1992, pp. 191-200, vol. 94.
Kandela et al., "Effect of the lipophilic/hydrophilic character of cationic triarylmethane dyes on their selective phototoxicity toward tumor cells", Biotechnic & Histochemistry, 2003, pp. 157-169, vol. 78, No. 3-4.
Kang et al., "Dose-dependent regulation of superoxide anion on the proliferation, differentiation, apoptosis and necrosis of human hepatoma cells: the role of intracellular Ca2+", Redox Report, 2004, pp. 37-48, vol. 9, No. 1.
Karl et al., "Cell Contraction Caused by Microtubule Disruption Is Accompanied by Shape Changes and an Increased Elasticity Measured by Scanning Acoustic Microscopy", Cell Biochemistry and Biophysics, 1998, pp. 225-241, vol. 29.
Karl et al., "Tension Modulates Cell Surface Motility: A Scanning Acoustic Microscopy Study", Cell Motility and the Cytoskeleton, 1999, pp. 349-359, vol. 43.
Katz et al., "Micromechanics of the Dentin/Adhesive Interface", Journal of Biomedical Materials Research, 2001, pp. 366-371.
Katz et al., "Scanning Acoustic Microscope Studies of the Elastic Properties of Osteons and Osteon Lamellae", Journal of Biomechanical Engineering, Nov. 1993, pp. 543-548, vol. 115.
Katz et al., "Scanning Acoustic Microscopy of Human and Canine Cortical Bone Microstructure at High Frequencies", Studies in Health Technology and Informatics, 1997, pp. 123-137, vol. 40.
Kim et al. "Development of polymeric nanoparticulate drug delivery systems: evaluation of nanoparticles based on biotinylated poly(ethylene glycol) with sugar moiety", International Journal of Pharmaceutics, 2003, pp. 195-203, vol. 257.
Kino et al., "Fundamentals of Scanning Systems", Scanned Image Microscopy, New York, Academic Press Inc.; 1980, pp. 1-21.
Kinoshita et al., "Evaluation of Acoustic Properties of the Live Human Smooth-Muscle Cell Using Scanning Acoustic Microscopy", Ultrasound in Medicine & Biology, 1998, pp. 1397-1405, vol. 24, No. 9.
Kirkpatrick et al., "Endogenous Fluorescence Spectroscopy of Cell Suspensions for Chemopreventive Drug Monitoring", Photochemistry and Photobiology, 2005, pp. 125-134, vol. 81.
Kobayashi et al., "Spectroscopic Imaging and the Characterization of the Autofluorescence Properties of Human Bronchus Tissues Using UV Laser Diodes", IEEE Journal of Selected Topics in Quantum Electronics, Mar./Apr. 2003, pp. 142-147, vol. 9, No. 2.
Kolodziejczyk et al., "Transmission acoustic microscopy of tissue sections (1 GHz). Histoacoustics and acoustic staining." Histochemistry, 1988, pp. 165-169, vol. 88.

Kostarelos et al., "Binding and Interstitial Penetration of Liposomes Within Avascular Tumor Spheroids", International Journal of Cancer, 2004, pp. 713-721, vol. 112.

Krasnici et al., "Effect of the Surface Charge of Liposomes on Their Uptake by Angiogenic Tumor Vessels", International Journal of Cancer, 2003, pp. 561-567, vol. 105.

Krishna et al., "Micro-Raman Spectroscopy for Optical Pathology of Oral Squamous Cell Carcinoma", Applied Spectroscopy, 2004, pp. 1128-1135, vol. 58, No. 9.

Kurachi et al., "Optical Biopsy for Detection of Chemical-Induced Tongue Lesions in Golden Syrian Hamsters: An in vivo Study", Laser Physics, 2004, pp. 502-506, vol. 14, No. 4.

Lamarque et al., "Acoustic Microscopy: A New Tool for Ultrasonic Breast Tissue Characterization", Europ. J. Radiol., 1983, pp. 221-222, vol. 3.

Lambert, "Diagnosis of Esophagogastric Tumors", Endoscopy, 2004, pp. 110-119, vol. 36.

Laochariyakul et al., "Functional study of intracellular P-gp- and MRP1-mediated pumping of free cytosolic pirarubicin into acidic organelles in intrinsic resistant SiHa cells", Canadian Journal of Physiology and Pharmacology, 2003, pp. 790-799, vol. 81.

Larson, "An Acoustic Transducer Array for Medical Imaging—Part I", Hewlett-Packard Journal, Oct. 1983, pp. 17-22, vol. 34.

Le At Al., "Plant-derived 3,3'-Diindolylmethane Is a Strong Androgen Antagonist in Human Prostate Cancer Cells", The Journal of Biological Chemistry, Jun. 2003, pp. 21136-21145, vol. 278, No. 23.

Lemons et al. "Acoustic Microscopy: Biomedical Applications", Science, May 1975, pp. 905-911, vol. 188, No. 4191.

Levinson, "Phase Detection in Acoustic Microscopy", Ultrasonic Imaging, 1990, pp. 292-308, vol. 12.

Li et al., "Improved Synthetic Aperture Focusing Technique with Applications in High-Frequency Ultrasound Imaging", IEEE Transactions on Ultrasonics, Ferroelectrics, and Frequency Control, Jan. 2004, pp. 63-70, vol. 51, No. 1.

Linker et al., "Autocorrelation Length of Normal and Myopathic Human Myocardium Measured by Acoustic Microscopy: Implications for Clinical Ultrasonic Tissue Characterization", Ultrasound in Medicine & Biology, 1990, pp. 793-799, vol. 16, No. 8.

Litniewski et al., "Measurements of cells in culture by scanning acoustic microscopy", Journal of Microscopy, Apr. 1990, pp. 95-107, vol. 158, Pt. 1.

Liu et al., "Synthesis and Cellular Studies of Nonaggregated Water-Soluble Phthalocyanines", Journal of Medicinal Chemistry, 2005, pp. 1033-1041, vol. 48.

Lovejoy et al., "Temperature dependence of minority and majority carrier mobilities in degenerately doped GaAs", Applied Physics Letters, Aug. 1995, pp. 1101-1103, vol. 67, No. 8.

Lu et al., "Evaluation of Progression in Nonrheumatic Aortic Valvular Stenosis by Scanning Acoustic Microscopy", Ultrasound in Medicine & Biology, 2000, pp. 563-569, vol. 26, No. 4.

Luers et al., "Acoustic Microscopy of Cultured Cells. Distribution of Forces and Cytoskeletal Elements", Cell Biophysics, 1991, pp. 279-293, vol. 18, Issue 3.

Macrae, "Rays of Hope. Spectroscopy as an Emerging Tool for Cancer Diagnostics and Monitoring", Spectroscopy, 2003, pp. 14-19, vol. 18.

Madhuri et al., "Native Fluorescence Spectroscopy of Blood Plasma in the Characterization of Oral Malignancy", Photochemistry and Photobiology, 2003, pp. 197-204, vol. 78, No. 2.

Manjunath et al., "Autofluorescence of oral tissue for optical pathology in oral malignancy", Journal of Photochemistry and Photobiology B: Biology, 2004, pp. 49-58, vol. 73.

Mark et al., "Fourier transform infrared microspectroscopy as a quantitative diagnostic tool for assignment of premalignancy grading in cervical neoplasia", Journal of Biomedical Optics, May/Jun. 2004, pp. 558-567, vol. 9, No. 3.

Markowitz et al., "Identification and Characterization of Small Molecule Inhibitors of the Calcium-Dependent S100B—p53 Tumor Suppressor Interaction", Journal of Medicinal Chemistry, 2004, pp. 5085-5093, vol. 47.

Marquez et al., "Charge-dependent Targeting: Results in Six Tumor Cell Lines", Anticancer Research, 2004, pp. 1347-1351, vol. 24.

Marquez et al., "Development of Dextran Derivatives with Cytotoxic Effects in Human Urinary Bladder Cancer Cell Lines", Anticancer Research, 2002, pp. 741-744, vol. 22.

Masilamani et al., "Cancer diagnosis by autofluorescence of blood components", Journal of Luminescence, 2004, pp. 143-154, vol. 109.

Masugata et al., "Evaluation of Left Atrial Wall Elasticity Using Acoustic Microscopy", Angiology, Jul. 1999, pp. 583-590, vol. 50, No. 7.

Masugata et al., "Relationship Between Myocardial Tissue Density Measured by Microgravimetry and Sound Speed Measured by Acoustic Microscopy", Ultrasound in Medicine & Biology, 1999, pp. 1459-1463, vol. 25, No. 9.

Masugata et al., "Tissue Characterization of Myocardial Cells by Use of High-Frequency Acoustic Microscopy: Differential Myocyte Sound Speed and Its Transmural Variation in Normal, Pressure-Overload Hypertrophic, and Amyloid Myocardium", Angiology, Oct. 1999, pp. 837-845, vol. 50, No. 10.

Mayinger et al., "Evaluation of Endoscopic Fluorescence Spectroscopy for Gastric Cancer", Gastroenterology, 2003, pp. A185-A185, vol. 124.

Mayinger et al., "Influence of Collagen in Endoscopic Fluorescence Spectroscopy for Gastric Cancer", Gastrolintestinal Endoscopy, 2004, p. P172, vol. 59, No. 5.

McPherson, "Tissue Characterization by Ultrasound: What is Possible Now? What Will be Possible?" Echocardiography, 1991, pp. 77-91, vol. 8, No. 1.

Mercer et al., "Metastatic breast cancer cells suppress osteoblast adhesion and differentiation", Clinical & Experimental Metastasis, 2004, pp. 427-435, vol. 21.

Miller et al., "The Determination of Very Small Electrophoretic Mobilities in Polar and Nonpolar Colloidal Dispersions Using Phase Analysis Light Scattering", Journal of Colloid and Interface Science, May 1991, pp. 532-554, vol. 143, No. 2.

Mizutani et al., "Evaluation of Acetic Acid-Induced Gastric Ulcers in Rats by Scanning Acoustic Microscopy", Scand J Gastroenterol, 1991, pp. 313-320, vol. 26.

Monici et al., "Dependence of leukemic cell autofluorescence patterns on the degree of differentiation", Photochemical & Photobiological Sciences, 2003, pp. 981-987, vol. 2.

Moussa et al., "Finite Element Modeling of Extraordinary Magnetoresistance in Thin Film Semiconductors with Metallic Inclusions", Physical Review B (Condensed Matter and Materials Physics), 2001, pp. 184410/1-184410/8, vol. 64.

Moxnes et al., "The dynamics of cell proliferation", Medical Hypotheses, 2004, pp. 556-563, vol. 62.

Muller et al. "Spectroscopic Detection and Evaluation of Morphologic and Biochemical Changes in Early Human Oral Carcinoma", Cancer, Apr. 2003, pp. 1681-1692, vol. 97, No. 7.

Munoz-Martinez et al., "Celastraceae Sesquiterpenes as a New Class of Modulators That Bind Specifically to Human P-Glycoprotein and Reverse Cellular Multidrug Resistance", Cancer Research, Oct. 2004, pp. 7130-7138, vol. 64.

Nadeau et al., "In vivo measurement of 5-aminolaevulinic acid-induced protoporphyrin IX photobleaching: a comparison of red and blue light of various intensities", Photodermatology Photoimmunology & Photomedicine, 2004, pp. 170-174, vol. 20.

Neild et al., "Images of arterioles in unfixed tissue obtained by acoustic microscopy", Journal of Microscopy, Jul. 1985, pp. 19-25, vol. 139.

Nomura et al., "Micromechanics/structure relationships in the human mandible", Dental Materials, 2003, pp. 167-173, vol. 19.

Office Action for EP Application 07874412.5 dated Jun. 9, 2010.

Office Action for EP Application 09010537.0 dated Nov. 15, 2010.

Ogawa et al., "Effect of Replacing the Aspartic Acid/Glutamic Acid Residues of Bullfrog Sialic Acid Binding Lectin with Asparagine/Glutamine and Arginine on the Inhibition of Cell Proliferation in Murine Leukemia P388 Cells", Biol. Pharm. Bull., 2002, pp. 722-727, vol. 25, No. 6.

Ortner et al., "Time gated fluorescence spectroscopy in Barrett's oesophagus", Gut, 2003, pp. 28-33, vol. 52.

Palmer et al., "Autofluorescence Spectroscopy of Normal and Malignant Human Breast Cell Lines", Photochemistry and Photobiology, 2003, pp. 462-469, vol. 78, No. 5.

Palmer et al., "Comparison of Multiexcitation Fluorescence and Diffuse Reflectance Spectroscopy for the Diagnosis of Breast Cancer (Mar. 2003)", IEEE Transactions of Biomedical Engineering, Nov. 2003, pp. 1233-1242, vol. 50, No. 11.

Panjehpour et al., "Laser-Induced Fluorescence Spectroscopy for in Vivo Diagnosis of Non-melanoma Skin Cancers", Lasers in Surgery and Medicine, 2002, pp. 367-373, vol. 31.

Panyam et al., "Rapid endo-lysosomal escape of poly(DL-lactide-co-glycolide) nanoparticles: implications for drug and gene delivery", The FASEB Journal, Aug. 2002, pp. 1217-1226, vol. 16.

Papo et al., "New Lytic Peptides Based on the D,L-Amphipathic Helix Motif Preferentially Kill Tumor Cells Compared to Normal Cells", Biochemistry, 2003, pp. 9346-9354, vol. 42, No. 31.

Park et al., "Multispectral digital microscopy for in vivo monitoring of oral neoplasia in the hamster cheek pouch of carcinogenesis", Optics Express, 2005, pp. 749-762, vol. 13, No. 3.

Partial European Search Report for EP Application 09010537.0 dated Feb. 24, 2010.

Primakoff et al., "Diffraction of Sound around a Circular Disk", The Journal of the Acoustical Society of Ameria, pp. 132-142, Jan. 1947, vol. 19, No. 1.

Qin et al., "Staining intensity of individual osteons correlated with elastic properties and degrees of mineralization", Journal of Bone and Mineral Metabolism, 2001, pp. 359-364, vol. 19.

Recchia et al., "Sensitive Detection of Abnormal Aortic Architecture in Marfan Syndrome With High-Frequency Ultrasonic Tissue Characterization", Circulation, 1995, pp. 1036-1043, vol. 91.

Rowe et al., "A Uniaxial Tensile Stress Apparatus for Temperature-Dependent Magnetotransport and Optical Studies of Thin Films", Review of Scientific Instruments, 2002, pp. 4270-4276, vol. 73, No. 12.

Rowe et al., "Enhanced Room-Temperature Piezoconductance of Metal-Semiconductor Hybrid Structures", Applied Physics Letters, 2003, pp. 1160-1162, vol. 83, No. 6.

Saijo et al., "Acoustic Properties of Atherosclerosis of Human Aorta Obtained with High-Frequency Ultrasound", Ultrasound in Medicine and Biology, 1998, pp. 1061-1064, vol. 24, No. 7.

Saijo et al., "Application of Scanning Acoustic Microscopy for Assessing Stress Distribution in Atherosclerotic Plaque", Annals of Biomedical Engineering, 2001, pp. 1048-1053, vol. 29.

Hays et al., "Hot-Electron Spectroscopy of GaAs", Physical Review Letters, 1985, pp. 1570-1572, vol. 54, No. 14.

International Preliminary Report on Patentability (Chapter I) for PCT/US20111020545 issued Jul. 19, 2012.

International Search Report and Written Opinion for PCT/US2011/020545 dated Aug. 29, 2011.

Law et al., "Nanoribbon Waveguides for Subwavelength Photonics Integration", Science, 2004, pp. 1269-1273, vol. 305.

Office Action for AU Application 2007349279 issued Jul. 28, 2011.

Office Action for U.S. Appl. No. 12/986,621 dated Nov. 19, 2012.

Palevski et al., "Lateral Tunneling, Ballistic Transport, and Spectroscopy in a Two-Dimensional Electron Gas", Physical Review Letters, 1989, pp. 1776-1779, vol. 62, No. 15.

Solin et al., "Geometry Driven Interfacial Effects in Nanoscopic and Macroscopic Semiconductor Metal Hybrid Structures: Extraordinary Magnetoresistance and Extraordinary Piezoconductance", Proc. of the International Symposium on Clusters and Nanoassemblies, 2003, Richmond.

Solin, "Magnetic Field Nanosensors", Scientific American, Jul. 2004, pp. 71-77, vol./No. 291(1).

Summons to Attend Oral Proceedings for EP Application 07874412.5 dated May 25, 2012.

Wieland et al., "Experimental Measurement and Finite-Element Modeling of Extraordinary Optoconductance in GaAs-In Metal-Semiconductor Hybrid Structures", Physical Review B, 2006, 155305, vol. 73.

Wieland et al., "Extraordinary optoconductance in metal-semiconductor hybrid structures", Applied Physics Letters, 2006, 052105, vol. 88.

Intention to Grant for EP07874412.5 dated Aug. 20, 2012.

Office Action for JP Application 2009-523015 dated Jan. 29, 2013.

MULTIFUNCTIONAL NANOSCOPY FOR IMAGING CELLS

CROSS-REFERENCE AND PRIORITY CLAIM TO RELATED PATENT APPLICATION

This patent application claims priority to U.S. provisional patent application 60/821,040, filed Aug. 1, 2006, and entitled "Multifunctional Nanoscopy for Imaging Cells", the entire disclosure of which is incorporated herein by reference.

STATEMENT REGARDING FEDERALLY SPONSORED RESEARCH OR DEVELOPMENT

This invention was made with government support under NIH grants such as EB002168, HL042950, and CO-27031 awarded by the National Institutes of Health (NIH). The government may have certain rights in the invention

FIELD OF THE INVENTION

The field of this invention relates generally to techniques for measuring characteristics of an object (such as the cell function and structure of one or more living cells) on a nanoscale via an array of integrated nanosensors that are responsive to various perturbations such as acoustic waves, light, or electric charge.

BACKGROUND AND SUMMARY OF THE INVENTION

The rapid acquisition and analysis of high volumes of data in biological samples had its advent in the early days of the human genome sequencing project. Microarray technology has facilitated the interrogation of large numbers of samples for biologically relevant patterns in a variety of physiological, drug-induced or clinically relevant cellular states. A challenge has now presented itself with respect to how these large volumes of information can be integrated into an accurate model of cellular behavior and processes. For example, information relating the effect of a drug to the extent and duration of apoptosis in cancer cells would be invaluable information in a screen for cancer drugs. Similarly, information of cytoskeletal changes leading to invasiveness would greatly streamline the development of an efficient anti-angiogenic drug strategy.

The discipline of cytomics has emerged to meet these and other demands in both the academic and industrial research communities. The importance of cytomics derives from the fact that the cell is the minimal functional unit within our physiology. An attendant technology to the emergence of cytomics is High Content Screening (HCS) which is generally defined as a simultaneous, or near real-time, multiparametric analysis of various aspects of cell state.

The complexity of cell function is only part of why cytomics will likely become a major field of study in the near future. Every cell is different, and by studying each cell's unique function, that cell type can be further modeled for subsequent analysis using statistical techniques. Within a short time, the inventors herein forecast that most pharmaceutical companies will not operate without encompassing the essential features of cytomics-drugs-design; a process that will increasingly operate at the level of modified cellular functions. Future cancer strategies may place greater emphasis on cytome-alignment or cytomic-realignment, which may be viewed as the "cellular form" of tissue engineering. Such an approach will require a better-than-ever understanding of how the cell operates, of how to measure cell function, and of how to characterize a live cell in minute detail. To meet this challenge, there is need in the art for the development of new technologies and new analytical tools for exquisitely sensitive single-cell analysis.

A primary goal of cytomics is the discovery of functional relationships between the cell (cytome) and the metabolic pathways (i.e., proteomics, which enables rapid identification of proteins from specific cell populations) resulting from genetic control mechanisms (i.e., genomics; some in the art relate cytomics to functional genomics). With cytomics, the amount of information being collected from the cell is expanded in order to obtain functional data, not just morphological, phenotypic, or genotypic data.

Currently, there are two major branches of cytomics: analytical cytology and image cytology. The first, analytical cytology, is comprised of traditional analytical techniques such as: flow cytometry, single cell analysis systems and tissue analysis (after cell separation). The second, image cytology (and analysis) is comprised of techniques such as "quantitative" fluorescence assays, high throughput cell culture assays (96-384-1536 well plates), drug effect assays of cytotoxicity, toxicology assays, apoptosis assays, cell proliferation assays, cell ploidy assays, and DNA array assays. These techniques are typically applied to single cells, tissues and sections, and cell culture systems in both 3D and 4D cell culture environments. Laser Scanning Cytometry (LSC) is a well-known example of this type of assay.

At the highest level, cytomics links technology to functional biology at the cellular level by relating measurement and detection to structure and function. To achieve this end, cytomics integrates tools like flow cytometry, image cytometry, etc. with proteomics and this brings together traditional cytometry and non-traditional cytometry. With the application of so many different measurement technologies to the same problem, informatics now assumes a primary rather than a secondary role in cytomics. For instance, in a typical flow cytometry system, there are 120,000 events per second per output channel, with measurements being acquired for multiple channels. Another example is offered by very high speed cell culture plate imaging systems applied to detect fluorescent markers in cells.

The term HCS is used to differentiate assays that use live cells and to provide single point readouts (e.g., High Throughput Screening (HTS) assays), which are often based on the biochemistry of ligand binding. HCS combines cell-based arrays with robotics, informatics, and advanced imaging to provide richly detailed information on cell morphology and other responses in large quantities.

Many protocols for generating data are already well developed in their respective disciplines, from quantitative Polymerase Chain Reaction (PCR), to flow cytometry, to antibody staining. The methods for acquisition of this data, such as different types of optical microscopy, have already undergone extensive development. Perhaps the most important image acquisition methods for HCS relate to cellular imaging, including drug effect assays for cytotoxicity, apoptosis, cell proliferation, and nucleocytoplasmic transport. Frequently, these approaches utilize cell sensors based on fluorescent proteins and dyes, and thus provide researchers with an ability to screen drugs and to answer more complex biological questions such as target identification and validation and to investigate gene and protein function.

In an effort to fill a need in the art for improved cellular imaging techniques, the inventors herein disclose a new, inexpensive, and easy-to-use imaging technology suitable for simultaneous capture of multiple measurements from individual cells that will enable molecular colocalization, metabolic state and motility assessment, and determination of cell cycle, texture, and morphology. This technology will be capable of not only HCS, but also permit selection of single cells for subsequent high-resolution imaging based on the outputs of the HCS. By increasing the analytical resolution to assess the sub-cellular state in vivo, the inventors herein hope to increase biological resolution by providing a means to follow the location, timing, and interdependence of biological events within cells in a culture.

The present invention builds upon the previous works by one of the inventors herein, wherein the extraordinary magnetoresistance (EMR) and extraordinary piezoconductance (EPC) properties of hybrid semiconductor/metal devices were used to develop improved sensing techniques for a wide variety of applications. For EMR devices, examples include but are not limited to read heads for ultra high density magnetic recording, position and rotation sensors for machine tools, aircraft and automobiles, flip phone switches, elevator control switches, helical launchers for projectiles and spacecraft, and the like. For EPC devices, examples includes but are not limited to a myriad of pressure sensors, blood pressure monitors, and the like. See U.S. patent application publication 2004/0129087 A1 entitled "Extraordinary Piezoconductance in Inhomogeneous Semiconductors", U.S. Pat. Nos. 6,714,374, 6,707,122, 5,965,283, and 5,699,215, Solin et al., *Enhanced room-temperature geometric magnetoresistance in inhomogeneous narrow-gap semiconductors*, Science, 2000; 289, pp. 1530-32; Solin et al., *Self-biasing nonmagnetic giant magnetoresistance sensor*, Applied Physics Letters, 1996; 69, p. 4105-4107; Solin et al., *Geometry driven interfacial effects in nanoscopic and macroscopic semiconductor metal hybrid structures: Extraordinary magnetoresistance and extraordinary piezoconductance*, Proc. of the International Symposium on Clusters and Nanoassemblies, Richmond, 2003; Rowe et al., *Enhanced room-temperature piezoconductance of metal-semiconductor hybrid structures*, Applied Physics Letters, 2003; 83, pp. 1160-62; Solin et al., *Non-magnetic semiconductors as read-head sensors for ultra-high-density magnetic recording*, Applied Physics Letters, 2002; 80, pp. 4012-14; Zhou et al., *Extraordinary magnetoresistance in externally shunted van der Pauw plates*, Applied Physics Letters, 2001; 78, p. 667-69; Moussa et al., *Finite element modeling of enhanced magnetoresistance in thin film semiconductors with metallic inclusions*, Physical Review B (Condensed Matter and Materials Physics) 2001; 64, pp. 184410/1-184410/8; Solin et al., *Room temperature extraordinary magnetoresistance of non-magnetic narrow-gap semiconductor/metal composites: Application to read-head sensors for ultra high density magnetic recording*, IEEE Transactions on Magnetics, 2002; 38, pp. 89-94; Pashlin et al., *Room-temperature Al single-electron transistor made by electron-beam lithography*, Applied Physics Letters, 2000; 76, p. 2256-58; Branford et al., *Geometric manipulation of the high field linear magnetoresistance in InSb epilayers on GaAs (001)*, Applied Physics Letters, 2005, 86, p. 202116/1-202116/3; and Rowe et al, *A uni-axial tensile stress apparatus for temperature-dependent magneto-transport and optical studies of epitaxial layers*, Review of Scientific Instruments, 2002; 73, pp. 4270-76, the entire disclosures of each of which being incorporated by reference herein.

The inventors herein extend upon the EMR and EPC sensors referenced above to disclose arrays comprised of a plurality of individual hybrid semiconductor/metal devices that can be used to measure voltage responses that are indicative of various characteristics of an object that is in proximity to the hybrid semiconductor/metal devices (such as one or more cells, either in vivo or in vitro) and from which images of the object characteristics can be generated. These hybrid semiconductor/metal devices may comprise a plurality of EXX sensors on a microscale or a nanoscale. Preferably, these EXX sensors comprise nanoscale EXX sensors. As used herein, "nanoscale" refers to dimensions of length, width (or diameter), and thickness for the semiconductor and metal portions of the EXX sensor that are not greater than approximately 1000 nanometers in at least one dimension. As used herein, "microscale" refers to dimensions of length, width (or diameter), and thickness for the semiconductor and metal portions of the EXX sensor that are not greater than approximately 1000 micrometers in at least one dimension. The term "EXX sensor" refers to a class of hybrid semiconductor/metal devices having a semiconductor/metal interface whose response to a specific type of perturbation produces an extraordinary interfacial effect XX or an extraordinary bulk effect XX. The interfacial or bulk effect XX is said to be "extraordinary" as that would term would be understood in the art to mean a many-fold increase in sensitivity relative to that achieved with a macroscopic device for the same perturbation. Examples of XX interfacial effects include the MR (magnetoresistance) and PC (piezoconductance) effects known from previous work by one of the inventors herein as well as EC (electroconductance) effects. It should be noted that AC (acoustoconductance) effects are effectively the same as the PC effects in that both the EAC and EPC devices can have identical structure. An EAC device can be thought of as a subset of a class of EPC devices, wherein the EAC device is designed to respond to a strain perturbation that is produced by an acoustic wave. An example of an XX bulk effect includes OC (optoconductance) effects. Thus, examples of suitable nanoscale EXX sensors for use in the practice of the present invention include nanoscale EMR sensors, nanoscale EPC sensors, nanoscale EAC sensors, nanoscale EOC sensors, and nanoscale EEC sensors.

The inventors herein believe that the use of nanoscale EAC sensors and nanoscale EPC sensors in an imaging array will provide improved imaging resolution, improved signal-to-noise ratio (SNR), and higher bandwidth than conventional ultrasonic or other modes of detectors. Accordingly, the use of an array having a plurality of nanoscale EAC sensors and/or a plurality of nanoscale EPC sensors can be used for a myriad of applications, including but not limited to in vitro cell imaging, in vivo invasive catheter-based applications for medical imaging, endoscopic imaging for gastrointestinal, prostate, or urethral/bladder/ureteral applications, transdermal medical imaging for disease characterization, detection of abnormal cells in serum samples, acoustic imaging, pressure sensing in nanofluidics, and blood pressure monitoring inside small vessels.

The inventors herein further believe that the use of nanoscale EOC sensors in an imaging array will produce ultra high resolution images of individual cells or tissues that are indicative of the presence of fluorescence in the cells/tissues, a result that can be highly useful in the investigation of cancer and cancer therapeutics, optical microscopy, photosensors and photodetectors, image intensifiers, position sensitive detectors, and position and speed control systems. The inventors further believe that additional uses for nanoscale EOC sensors in an imaging array include their use in static charge detection, EM radiation sensors, and EKG sensors.

The inventors herein further believe that the use of nanoscale EEC sensors in an imaging array will produce ultra high resolution images of electric charge distribution over the surface of one or more living cells, a result that can provide valuable information for monitoring cancer metastasis and targeted drug delivery, particularly so when a series of such images are taken over time to track the progression of the cell's electric charge over time. The inventors herein believe that the nanoscale EEC sensors of the present invention will serve as a significantly more accurate and effective measure of cell electric charge than the conventional electrophoresis technique that is known in the art because electrophoretic measurements suffer from a complicated instrumental dependence and a lack of spatial resolution.

The inventors herein further believe that the use of nanoscale EMR sensors in an imaging array will produce ultra high resolution images of magnetoresistance over the surface of one or more living cells, a result that can provide valuable information for studying the magnetic fields produced by nonmagnetic particles embedded in cancer cells, for monitoring magnetically labeled nanoparticles that are trafficking inside the cells or for sensing the evolution of imposed magnetic resonance spin orientations.

As perhaps the most powerful embodiment of the present invention, the inventors herein envision that a multi-modal array having a plurality of different types of EXX sensors can be used to simultaneously (or nearly simultaneously) generate multiple images that are representative of different characteristics of one or more cells that are imaged by the array. For example, with a multi-modal array having a plurality of EOC sensors and a plurality of EEC sensors, multiple images can be simultaneously generated that are representative of both fluorescent emissions by the cell(s) and the surface charge of the cell(s). Such images would exhibit a nanoscale resolution. As used herein, the term "type" as used in connection with EXX sensors refers to the type of XX interfacial effect or bull effect relied upon by the sensor. For example, an EAC sensor is of a different type than an EEC sensor.

The inventors further note that the ultra high resolution images produced in the practice of the present invention can not only be two-dimensional images, but optionally can also be three-dimensional images through the use of confocal imaging techniques.

These and other features and advantages of the present invention will be described hereinafter to those having ordinary skill in the art.

BRIEF DESCRIPTION OF THE DRAWINGS

FIG. 7($b$) illustrates a voltage response calculation for an EOC sensor that is partially covered to achieve nonuniform illumination as determined for different voltage lead geometries;

FIG. 7($c$) illustrates a plot of a voltage response and an EOC response for a uniformly illuminated EOC sensor and a bare semiconductor device as a function of the ratio $Y_{max}/X_{max}$;

FIG. 12($b$) is a perspective view of the array of FIG. 12($a$);

FIG. 14($b$) is a top view of a pixel corresponding to a plurality of different types of nanosensors;

FIG. 16($b$) is a perspective view of the array of FIG. 16($a$);

DETAILED DESCRIPTION OF THE PREFERRED EMBODIMENTS

Figure 1:
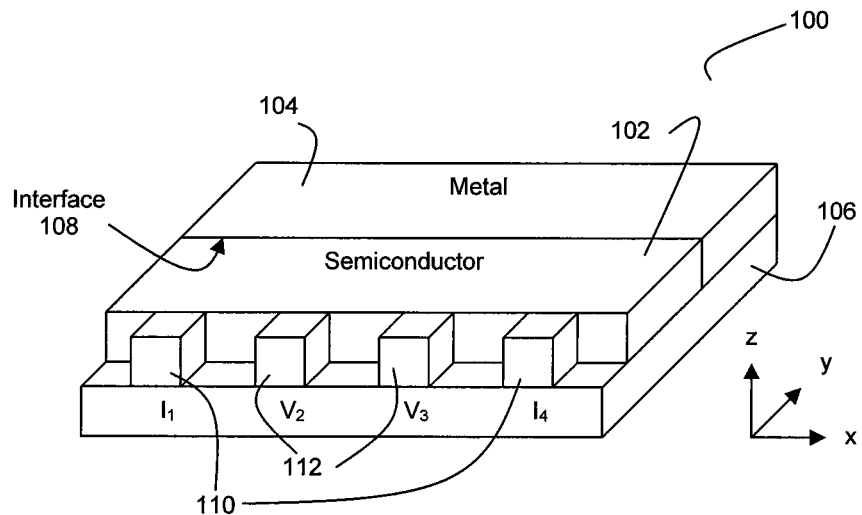
FIG. 1 is a perspective view of an exemplary EMR/EPC/EAC/EOC sensor.

FIG. 1 illustrates a preferred architecture for a nanoscale EXX sensor 100 of the types EMR, EPC, EAC, and EOC. As shown in FIG. 1, nanosensor 100 is a hybrid semiconductor/metal device comprising a semiconductor portion 102 and a metal shunt portion 104. The semiconductor 102 and the metal shunt 104 are disposed on a substrate 106. Together, the semiconductor portion 102 and the metal shunt portion 104 define a semiconductor/metal interface 108. Preferably, the semiconductor portion 102 and the metal shunt portion 104 are substantially co-planar as shown in FIG. 1. Furthermore, the semiconductor portion 102 and metal shunt portion 104 preferably lie in a substantially parallel plane as the substrate 106. Also, the plane of the semiconductor/metal interface 108 is preferably substantially perpendicular to the plane of the substrate 106. The architecture of the nanosensor 100 of FIG. 1 is referred to as an externally shunted van der Pauw (vdP) plate.

The semiconductor portion 102 is preferably a thin semiconductor film having a thickness of approximately 1000 nm. However, it should be understood that other thickness values can be used, for example a thickness in a range between approximately 25 nm and approximately 2000 nm. Furthermore, the semiconductor film 102 preferably has a length of approximately 100 nm and a width of approximately 50 nm. However, it should be noted that other lengths and widths for the semiconductor film can be used, for example any nanoscale value with a lower limit only bounded by lithography capabilities (currently believed to be around 5 nm, but this lower limit may further decrease with the passage of time and improvements in technology). As used herein, the term "thickness" will refer to the dimension along the z-axis as shown in FIG. 1, the term "length" will refer to the dimension along the y-axis as shown in FIG. 1, and the term "width" will refer to the dimension along the x-axis as shown in FIG. 1.

The dimensions for the metal shunt 104 can be a thickness of approximately 1000 nm, a length of approximately 100 nm, and a width of approximately 100 nm. However, it should be understood that (1) other thickness values could be used, for example a thickness within a range of approximately 25 nm to approximately 2000 nm, and (2) other lengths and widths could be used, for example any nanoscale length or width whose minimum value is only restricted by available lithography techniques, as noted above. It should also be noted that the dimensions of the metal shunt 104 relative to the semiconductor film 102 are expected to be continuously variable, and this relationship defines the filling factor for the device. Also, relative to the dimensions of the semiconductor film 102, it should be noted that the width of the shunt is typically less than or equal to the width of the semiconductor film. Typically, the thickness of the shunt will be the same as the thickness of the semiconductor film, although the shunt may be thinner than the semiconductor film (normally the shunt would not be thicker than the semiconductor film).

Preferably, the dimensions of the substrate 106 are much larger than the semiconductor film and metal shunt. The dimensions for the substrate 106 are preferably a thickness of approximately 400 μm and a diameter of approximately 2 inches. However, it should be understood that these values can vary considerable based upon the design choices of a practitioner of the invention.

The nanosensor 100 also preferably includes two current leads 110 and two voltage leads 112. These leads contact the semiconductor film 102 but not the metal shunt 104. Also, these leads preferably contact the semiconductor film 102 on a surface opposite the semiconductor/metal interface 108, as shown in FIG. 1. With respect to the geometry of the leads, the two voltage leads 112 are preferably disposed between the two current leads 110 as shown in FIG. 1. Furthermore, the spacing between leads is preferably selected in a manner to maximize the extraordinary magnetoresistance/piezoconductance/acoustoconductance/optoconductance effect of the nanosensor 100.

The use of the architecture of FIG. 1 as an EMR sensor and an EPC sensor is known in the art, as explained in the patents and publications cited above and incorporated by reference herein. However, their principles of operation will be briefly re-iterated. The 4-lead effective resistance of the hybrid semiconductor/metal device 100 of FIG. 1 is $R_{eff}=V_{23}/I_{14}$, wherein I and V represent the current and voltage leads 110 and 112 respectively. The value of $R_{eff}$ will depend on the relative conductivities of the metal 104 and semiconductor 102 (typically, $\sigma_{metal}/\sigma_{semiconductor}>1000$), on the resistance of the interface 108, and on the specific placement of the current and voltage leads (the lead geometry). When the hybrid semiconductor/metal device 100 is in a non-perturbed state, the highly conductive metal acts as an effective current shunt, provided that the resistance of interface 108 is sufficiently low, and $R_{eff}$ can be close to that of the metal. However, with a relatively small perturbation such as a change in the magnetic field, pressure/strain or temperature applied to the hybrid semiconductor/metal device 100, a significant change can be induced in the bulk resistance of the semiconductor 102 and/or the interface 108 resistance, and concomitantly the current flow across the interface 108 will be significantly altered. These induced changes will manifest themselves as a relatively large change in $R_{eff}$ which can then be easily measured via the output voltage signal from the voltage leads 112 when a current flow is provided to the hybrid semiconductor/metal device 100 via current leads 110.

Figure 2:
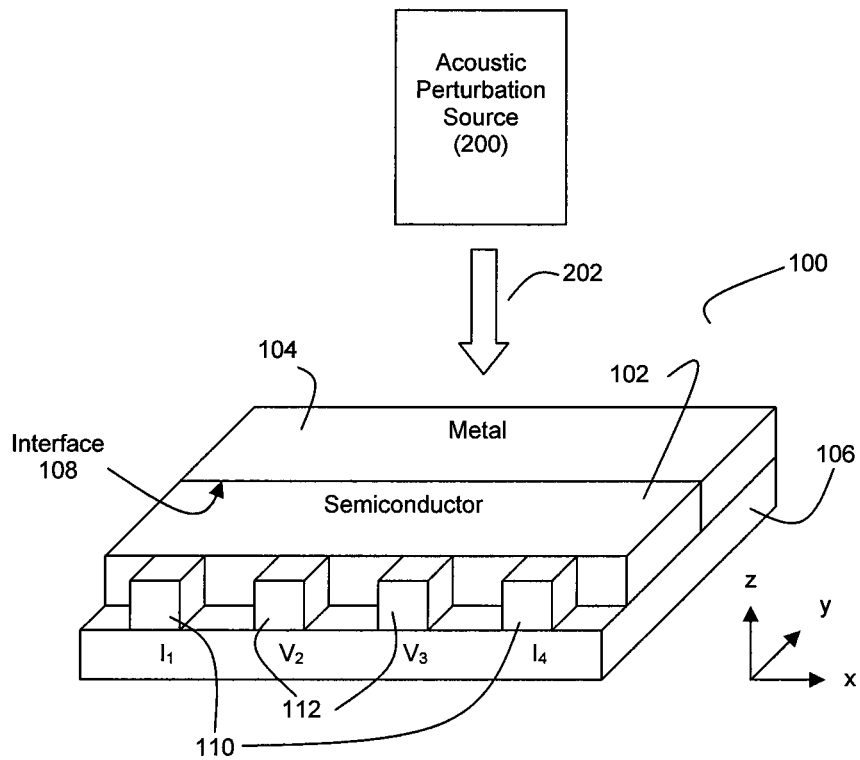
FIG. 2 is a perspective view of an exemplary EAC sensor that is perturbed by an acoustic perturbation source.

FIG. 2 illustrates a use of the sensor 100 of FIG. 1 as an EAC sensor. With an EAC nanosensor, the perturbation that results in the measurable voltage response is an acoustic wave 202. The acoustic wave 202 from an acoustic perturbation source 200 generates a strain at the interface 108 that results in a measurable voltage via the extraordinary piezoconductance effect. In this manner, the EAC sensor is highly similar to the EPC sensor. Preferably, the direction of the acoustic wave 202 is generally along the z-axis (or perpendicular to the plane of the semiconductor film 102 and metal shunt 104 or substantially in the same plane as the plane of the interface 108).

With an EAC/EPC sensor, the semiconductor/metal interface 108 produces a Schottky barrier to current flow. A tensile (compressive) strain along the direction of the interface 108 increase (decreases) the interatomic spacing, thereby increasing (decreasing) the barrier height. Because the tunneling current through the barrier depends exponentially on the barrier height and any change in that tunneling current is amplified by the EAC geometry, a small strain results in a large voltage change/signal. Experimentation by the inventors has shown that the piezoconductance is largest for an EPC sensor whose geometry is characterized by a filling factor of 9/16. See U.S. patent application publication 2002/0129087 A1.

Examples of acoustic perturbation sources that can be used in the practice of the invention include scanning acoustic microscopes (SAMs), ultrasound emitters using synthetic aperture focusing (SAFT), medical imagers with phased array transducers or single element focused or unfocused ultrasound transducers, shock wave devices, mid-to-high intensity focused ultrasound arrays, or alternative sources that are capable of inducing mechanical waves in cells and tissues. As examples, the characteristics of the acoustic perturbation can be as follows: a frequency across the ultra high frequency (UHF) band (300 MHz to 3 GHz, with corresponding wavelengths between 5 μm and 500 nm), a frequency in the lower portions of the super high frequency (SHF) band (3 GHz to 30 GHz, with corresponding wavelengths from 500 nm to 50 nm).

Figure 3:
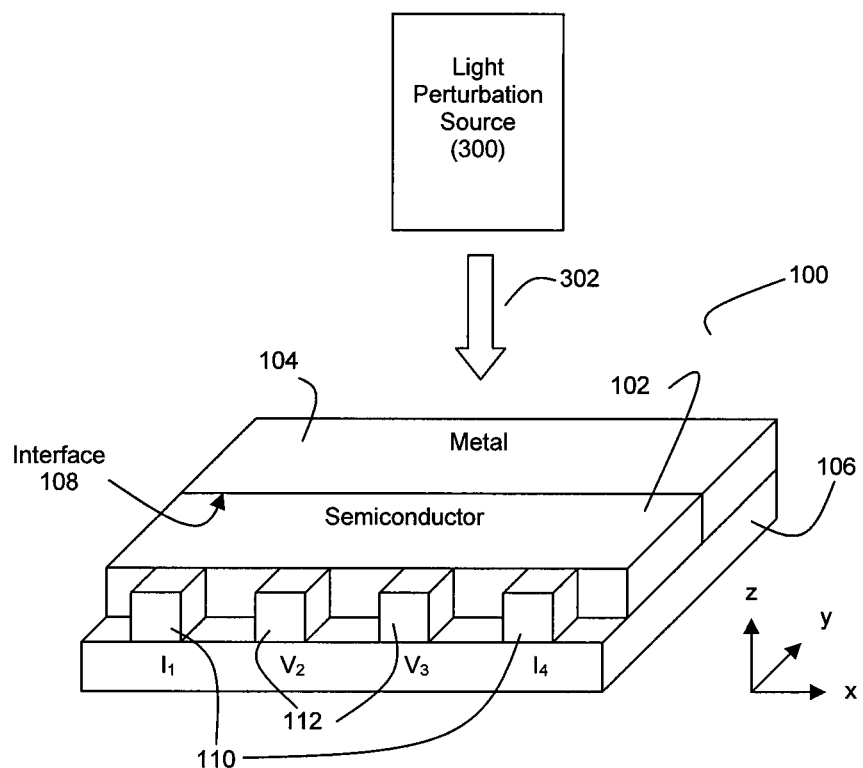
FIG. 3 is a perspective view of an exemplary EOC sensor that is perturbed by a light perturbation source.

FIG. 3 illustrates a use of the sensor 100 of FIG. 1 as an EOC sensor. With an EOC nanosensor, the perturbation that results in the measurable voltage response is light 302. The light 302 from a light perturbation source 300 that impacts the light exposed surfaces of the semiconductor film 102 and metal shunt 104 results in a measurable voltage via the extraordinary optoconductance effect. Preferably, the direction of propagation for the light 302 is generally along the z-axis (or perpendicular to the plane of the semiconductor film 102 and metal shunt 104 or substantially in the same plane as the plane of the interface 108). However, as noted below, as the size of the EOC nanosensor decreases, the light will more uniformly illuminate the EOC nanosensor due to the EOC nanosensor's small size.

The light perturbation source 300 can be any source of light emissions, such as a laser emitting device or even a cell with fluorescent emissions (such as would be emitted with the introduction of a fluorine-based contrast agent). Further still, the perturbing light can be electromagnetic radiation, spanning infrared to ultraviolet ranges, with wavelengths measured in the hundreds of nanometers.

Figure 4:
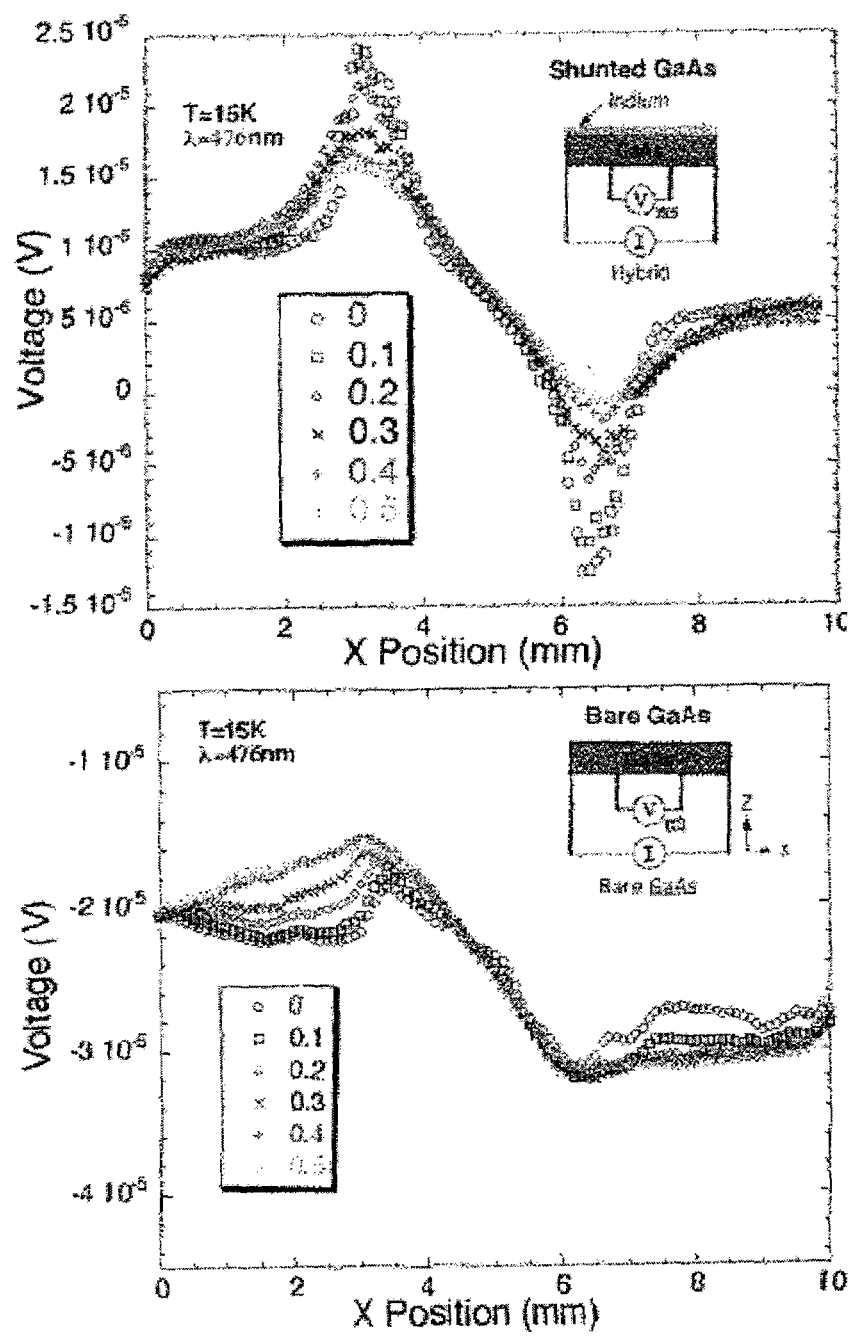
FIG. 4 depicts graphs that compares the optoconductance of a shunted GaAs/In EOC sensor versus a bare GaAs sensor.

FIG. 4 depicts (1) the photo response of a macroscopic GaAs—In semiconductor-metal hybrid EOC sensor 100 (wherein the semiconductor film 102 comprises GaAs and the metal shunt 104 comprises In) (upper panel) when exposed to a focused Ar ion laser beam of wavelength 476 nm, diameter 10 μm and power 5 mW at 15K, and (2) the photo response of macroscopic bare GaAs (without the In shunt) (lower panel)

to the same laser radiation. FIG. 4 plots the optoconductance versus a scan position of the laser beam along the x-axis of the EOC sensor 100 for a plurality of discrete scan z positions, wherein the x and z directions are characterized by the insets of FIG. 4. The panels of FIG. 4 illustrate three noteworthy characteristics of the EOC sensor: (1) the output voltage signal amplitude peaks near the voltage probes 112 (see the peaks in the voltage response at locations on the x-axis corresponding to the locations of the voltage probes 112), (2) the voltage response is much larger (~500%) for the shunted EOC sensor than for the bare GaAs (thereby demonstrating the EOC effect), and (3) the output voltage signal amplitude decreases as the focal spot of the laser moves in the z-direction toward the In shunt (which translates to the y-axis direction in the sensor 100 of FIG. 3).

These EOC effects can be understood as follows. The laser perturbation is absorbed by the semiconductor film 102 and creates a very high density of electron-hole pairs that is much larger than the ambient "dark" density. Because the electrons have a much higher mobility, and therefore a much large mean free path than the holes, the electrons are effectively shorted to ground by the metal shunt 104, leaving a positively charged region of excess holes that extends radially outward from the center of the impacting laser beam on the surface of the sensor 100. This excess positive charge creates an additional electric field at the voltage leads 112 which results in an enhanced signal as the laser beam passes the probes 112 along the X-direction. However, as the region of excess positive charge moves closer to the shunt 104 along the Z-direction (or y-axis of FIG. 3), more and more of the holes are also shorted to ground and the excess decreases. This results in a decrease in signal with increasing Z direction laser impact. An additional contribution to this decrease comes from the drop off in the excess hole induced electric field at the voltage contact with the Z direction distance of the laser spot from those voltage contacts. When there is no shunt 104 present, the electrons cannot be effectively shorted to ground and the amount of excess positive (hole) charge in the region of the laser spot is significantly reduced.

Figure 5:
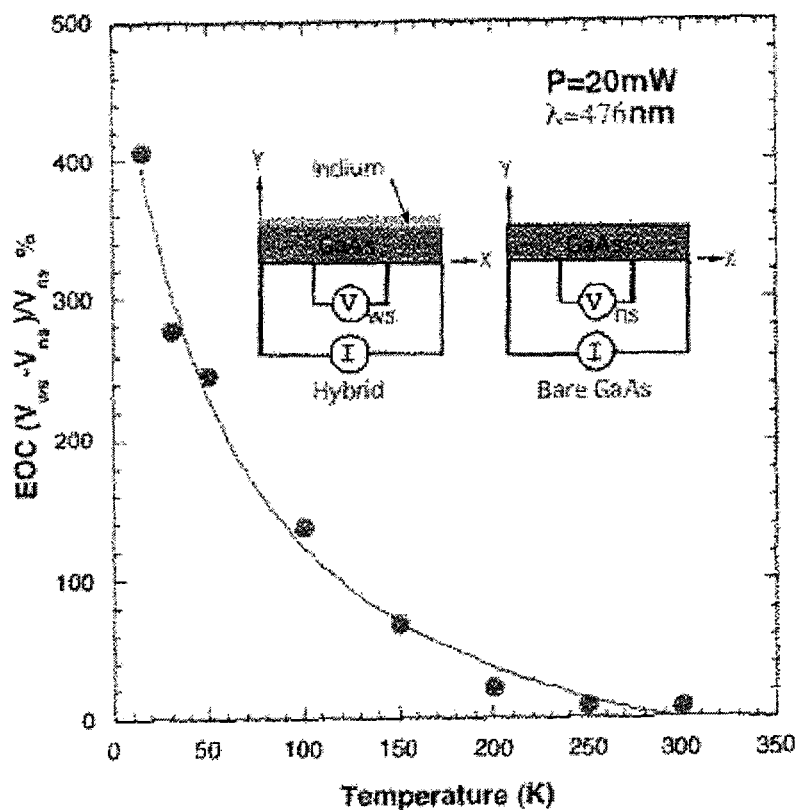
FIG. 5 is a graph depicting the temperature dependence of the EOC effect observed in a GaAs/In EOC sensor.

FIG. 5 plots the temperature dependence of the EOC effect for the sensors of FIG. 4. For the GaAs devices, the EOC effect is most pronounced at low temperatures because it is at these temperatures that the mean free path of the excess electrons is sufficiently long for them to reach and be shunted by the metal shunt 104. The carrier mean free path is proportional to the carrier mobility which is temperature independent and varies inversely with temperature for holes. The plot of FIG. 5 also shows a least squares fit to the data with a function that varies as 1/T where T is the sample temperature in degrees K, thereby indicating the temperature dependence of the EOC effect. On the basis of this analysis, we conclude that by using a direct gap but narrow gap semiconductor (such as InSb; the room temperature mobility of which is 70 times that of GaAs) and/or a nanoscopic structure for the EOC sensor, the EOC effect should be realizable at room temperature.

Also, to alleviate any thermal drifts of the output voltage, the InSb semiconductor can be doped with Si or Te donors so that an extrinsic carrier concentration in the saturation (e.g., temperature independent) range is achieved.

Also, the inventors note that as the size of the EOC sensor decreases, a point will be reached where the illumination caused by the light perturbation source becomes effectively uniform over the EOC sensor. This uniformity would operate to effectively integrate the plot of FIG. 4 over the X position, which results in a significant decrease in the strength of the voltage response from the EOC sensor.

Figure 6:
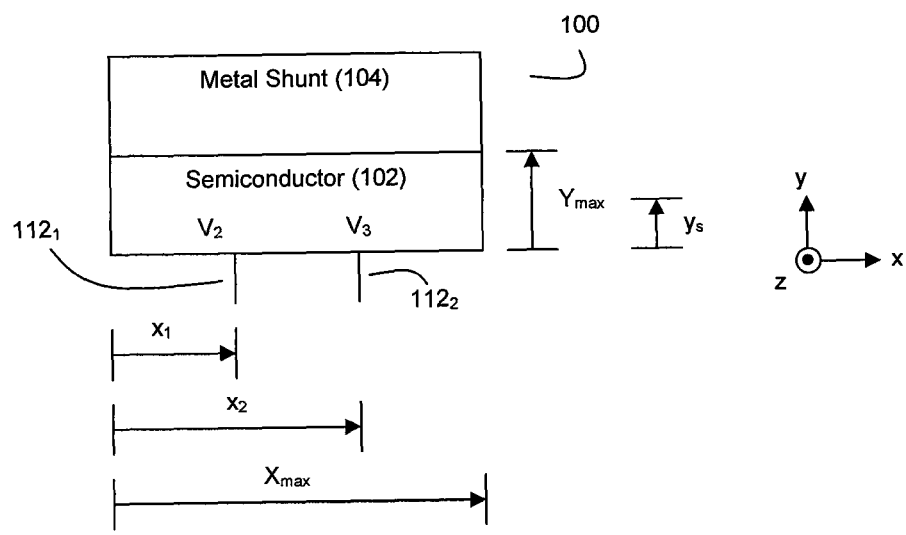
FIG. 6 depicts a top view of an exemplary EOC sensor showing how lead geometry can be adjusted.

One solution to this problem is to asymmetrically position the leads 110 and/or 112 along the x-axis. In one embodiment, such asymmetrical positioning can be achieved by asymmetrically positioning only the voltage leads 112 along the x-axis. FIG. 6 depicts a top view of an exemplary EOC sensor 100 showing the semiconductor portion 102, the metal shunt portion 104, and the voltage leads $112_1$ and $112_2$ (corresponding to the leads $V_2$ and $V_3$ from FIG. 3 respectively). The positions of the voltage leads 112 along the x-axis are shown in FIG. 6, wherein the full distance along the x-axis for the semiconductor 102 is shown by $X_{max}$. Using the leftmost position along the x-axis in FIG. 6 as the origin and the rightmost position along the x-axis as the value $X_{max}$, it can be seen that the x-axis position of voltage lead $112_1$ is represented by $x_1$, and that the x-axis position of voltage lead $112_2$ is represented by $x_2$. The voltage leads are said to be symmetrical if $x_1$ and $x_2$ exhibit values such that $x_2 = X_{max} - x_1$. To improve the voltage response of the EOC sensor 100, it is preferred that the voltage leads 112 be asymmetrically positioned along the x-axis.

The voltage potential $V_{23}$ between voltage leads $112_1$ and $112_2$ shown in FIGS. 3 and 6 can be calculated as the integral of the surface charge density over the distance to the charge:

$$V_{23}(x_1, x_2) = \frac{1}{4\pi\varepsilon_0} \int_0^{X_{max}} \int_0^{Y_{max}} \sigma(y) \left[ \frac{1}{\sqrt{(x-x_1)^2 + y^2}} - \frac{1}{\sqrt{(x-x_2)^2 + y^2}} \right] dx\, dy$$

wherein $Y_{max}$ is the length along the y-axis for the semiconductor portion 102, wherein $\sigma(y)$ represents the surface charge density, and wherein $\varepsilon_0$ represents the permittivity of free space. The surface charge density $\sigma(y)$ can be modeled in any of a number of ways. For example, in one model, the assumption is made that uniform illumination creates a uniform charge density, which could be represented as:

$$\sigma(y) = C_{total}\left(1 + \frac{1}{2}\theta(y - y_s)\right)$$

wherein $C_{total}$ represents the total charge, wherein $\theta$ represents the step (Heaviside) function, wherein the factor ½ is derived from the fact that proximity to the shunt 104 increases the net positive charge as the more mobile electrons are taken to ground more effectively, and wherein the parameter $y_s$ (see FIG. 6) reflects the intrinsic differential mobility of the material of interest. A large value of $y_s$ would indicate that all of the mobile carriers have access to ground via the shunt 104, while a small value of $y_s$ would indicate that a limited number of the mobile carriers have access to ground via the shunt. In this model, $y_s$ can be the distance along the y-axis as shown in FIG. 6 over which it is assumed that the electrons are effectively shunted to ground.

Another model can be made for the surface charge density by fitting $\sigma(y)$ to experimentally measured $V_{23}(y)$ data. In an experiment where $V_{23}$ was measured for an EOC sensor 100 employing degenerately doped GaAs that is exposed to a focused laser spot for the values of $X_{max}$=10 mm, $x_1$=3.4 mm, $x_2$=6.6 mm, and $Y_{max}$=1 mm, the $V_{23}$ values for different values of $x_1$ and $x_2$ can be calculated using the formula above for $V_{23}$ with x and y limits of integration over a 40 μm square (which approximates lengths corresponding to the diameter of the laser spot). Because the resultant $V_{23}$ data from such an experiment indicates that $V_{23}(y)$ is approximately Gaussian, the integrand in the formula above for $V_{23}$ must be of the form: $y*\exp(-y^2)$. Taking in mind a 1/y positional dependence, one can solve for the experimentally fit $\sigma(y)$ as follows:

$$\sigma(y)^{fit} = C_{total}\left(y + y^2 e^{-\left(\frac{y-y_h}{r_h}\right)}\right)$$

The effective radii of the Gaussian fit, $r_h$, can be 1.5 mm, with an offset $y_h$ of −0.88 mm.

Figure 7A:
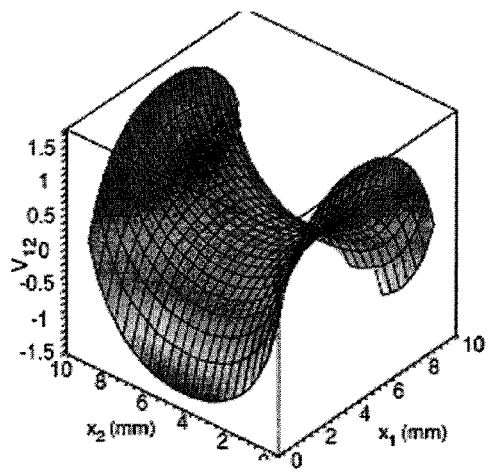
FIG. 7($a$) illustrates a voltage response calculation for a uniformly illuminated EOC sensor as determined for different voltage lead geometries.

The plot of FIG. 7(a) depicts the calculated voltage output $V_{23}$ of the EOC sensor 100 assuming a uniform charge density, a fixed $y_s$ of 0.5 mm, and a $Y_{max}/X_{max}$ ratio of 1/10. The different lead positions $x_1$ and $x_2$ are displayed on the xy plane and the voltage is displayed on the ordinate. In this plot, the symmetry of the voltage response is apparent. In this plot, the optimal lead position can be defined as the $(x_1, x_2)$ positions of (0 mm, 5 mm) and (10 mm, 5 mm) where the voltage response is at maximum. These positions, with one lead in the middle of the $X_{max}$ distance and the other lead at either end of the $X_{max}$ distance, can be understood qualitatively as the middle lead being closest to the most charge compared to the lead on the edge that has access to the least charge.

It should also be noted that in another embodiment, asymmetrical lead positioning can be achieved by asymmetrically positioning only the current leads 112 along the x-axis. Further still, it should be noted that asymmetrical lead positioning can also be achieved by asymmetrically positioning both the current leads 110 and the voltage leads 112 along the x-axis.

Figure 8A:
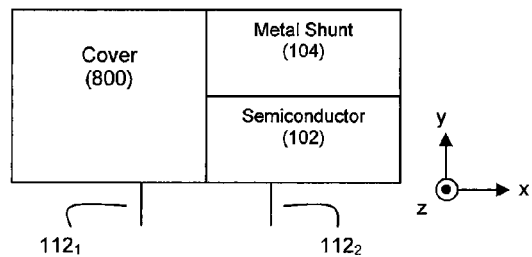
FIGS. 8($a$) and ($b$) depict a top view and side view for an exemplary EOC sensor having a cover to block light from illuminating a portion of the EOC sensor.
Figure 8B:
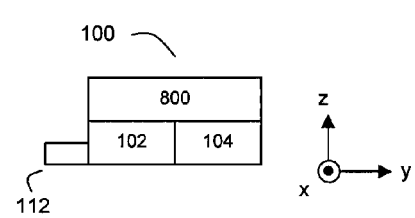

Another solution to the uniform illumination problem is to shield a portion of the EOC nanosensor that would be exposed to the light perturbation using a cover 800, as shown in FIGS. 8(a) (top view) and 8(b) (side view). In this way, nonuniform illumination can be achieved by blocking some of the light from perturbing the exposed surfaces of the semiconductor 102 and metal shunt 104. For example, cover 800 can be used to block half of the otherwise exposed surfaces of the semiconductor 102 and metal shunt 104. Cover 800 can be formed from materials such as a thin film (e.g., 20 nm) layer of an insulator (e.g., $SiO_2$) for a bottom surface of the cover 800 followed by a thicker layer (e.g., 50 nm or more) of any metal as an exposed surface of the cover 800. As another example, cover 800 can be formed from a single layer (e.g., a 50 nm layer) of any opaque insulator.

Figure 7B:
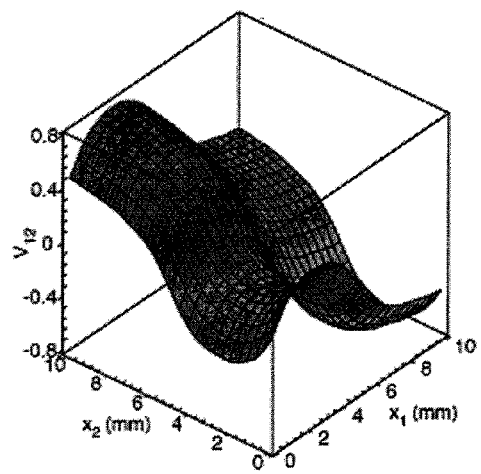

The plot of FIG. 7(b) depicts the calculated voltage output $V_{23}$ of the EOC sensor 100 assuming a uniform charge density, a fixed $y_s$ of 0.5 mm, and a $Y_{max}/X_{max}$ ratio of 1/10, wherein a cover 800 is used to block half of the exposed surface of the EOC sensor 100. The different lead positions $x_1$ and $x_2$ are displayed on the xy plane and the voltage is displayed on the ordinate. As can be seen, symmetrical leads can be used without the degradation that one finds in the plot of FIG. 7(a).

Figure 7C:
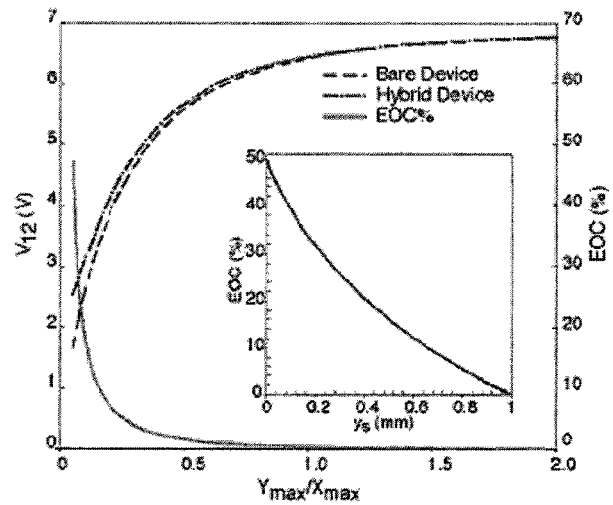

Another geometric parameter that is result-effective to increase the voltage response of the EOC sensor under uniform illumination is the ratio $Y_{max}/X_{max}$. This can be seen by way of example in FIG. 7(c). FIG. 7(c) depicts a plot of a calculated output voltage from a uniformly illuminated EOC sensor as a function of the ratio $Y_{max}/X_{max}$. FIG. 7(c) also depicts a plot of an EOC response, wherein the EOC response is defined as the percent difference in the measured output voltage of the EOC sensor as compared to that of a bare semiconductor sensor. FIG. 7(c) also depicts the voltage response for the bare device as a function of the ratio $Y_{max}/X_{max}$.

Figure 9:
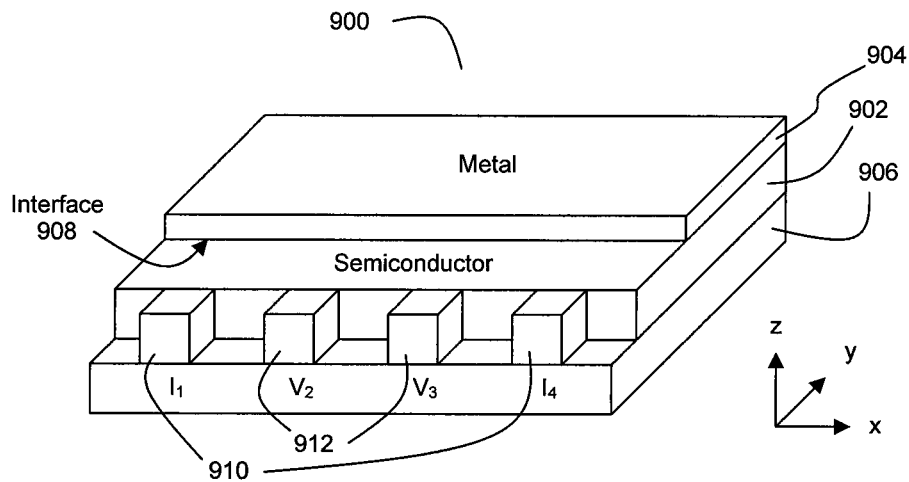
FIG. 9 is a perspective view of an exemplary EEC sensor.

FIG. 9 illustrates a preferred architecture for a nanoscale EEC sensor 900. As shown in FIG. 9, nanosensor 900 is a hybrid semiconductor/metal device comprising a semiconductor portion 902 and a metal shunt portion 904. The metal shunt portion 904 is disposed on a surface of the semiconductor portion 902, and the semiconductor portion 902 is disposed on a surface of substrate 906 such that the semiconductor portion 902 is sandwiched between the metal shunt portion 902 and the substrate 906. As shown in FIG. 9, the metal shunt portion 904, the semiconductor portion 902, and the substrate portion 906 preferably lie in substantially parallel planes. Together, the contact between the metal shunt portion 904 and the semiconductor portion 906 define a semiconductor/metal interface 908. Thus, unlike the nanosensor 100 of FIG. 1, the plane of the semiconductor/metal interface 908 of nanosensor 900 is substantially parallel with the plane of the metal shunt/semiconductor/substrate.

The semiconductor portion 902 is preferably a thin semiconductor film having a thickness of approximately 1000 nm. However, it should be understood that other thickness values can be used, for example a thickness in a range between approximately 25 nm and approximately 2000 nm, wherein the thickness value is selected to reduce the input resistance for an improvement in thermal noise reduction and signal-to-noise ratio. Furthermore, the semiconductor film 902 preferably has a length of approximately 100 nm and a width of approximately 50 nm. However, it should be noted other nanoscale length and width values of the semiconductor film 902 can be used, for example nanoscale length and widths whose lower limit is only bounded by lithography capabilities.

The dimensions for the metal shunt 904 are preferably a thickness of approximately 1000 nm, a length of approximately 100 nm, and a width of approximately 50 nm. For an EEC nanosensor, the width and length of the metal shunt 904 are preferably less than or equal to and do not exceed those of the semiconductor film 902. However, it should once again be understood that other thicknesses can be used (for example, any value within a range of approximately 25 nm to approximately 2000 nm, wherein the thickness value is selected to reduce the input resistance for an improvement in thermal noise reduction and signal-to-noise ratio). Also, the shunt's nanoscale length and width can also be other values selected so as to not exceed the length and width of the semiconductor film, with the lower limit bounded only by lithography capabilities.

Preferably, the dimensions of the substrate 906 are sized appropriately to support the dimensions of the semiconductor film 902, and as such the substrate 906 is typically much larger than the semiconductor film and metal shunt. Exemplary dimensions for the substrate 906 are preferably a thickness of approximately 400 μm and a diameter of approximately 2 inches. However, it should be understood that other dimensions could be used.

The nanosensor 900 also preferably includes two current leads 910 and two voltage leads 912. These leads contact the semiconductor film 902 but not the metal shunt 904. Also, these leads preferably contact the semiconductor film 902 on a surface along the xz thickness of the semiconductor film 902, as shown in FIG. 9. With respect to the geometry of the leads, the two voltage leads 912 are preferably disposed between the two current leads 910 as shown in FIG. 9. Furthermore, the spacing between leads is preferably selected in a manner to maximize the extraordinary electroconductance effect of the nanosensor 900.

With the EEC nanosensor of FIG. 9, in the absence of an external perturbing electric field, bias current entering at current lead $I_1$ and exiting a current lead $I_4$ will flow primarily through the metal shunt 904 due to its much higher conductivity than the semiconductor film 902. However, to access the metal shunt 904, this current must, for the proper choice of materials, tunnel through the Schottky barrier at the interface 908. This tunneling current varies exponentially with the external bias that is applied to the barrier. Thus, if a perturbing electric field impacts the interface 908 (such as the surface charge of a cancer cell that is deposited on the surface of the EEC sensor), then the perturbing electric charge will be normal to the interface 908. This perturbing field will cause a redistribution of the surface charge on the metal shunt 904, which will result in a bias field applied to the Schottky barrier. The resultant exponential change in tunneling current will result in the reapportionment of current flow between the semiconductor 902 and the metal shunt 904, which will result in a large detectable change in the voltage measured between voltage leads 912.

The inventors have estimated the magnitude of the electric field that one can expect from a cancer cell as follows. A claim is commonly made that normal cell in vivo have a negative charge, and values between −100 to −10 mV (which does not have the correct units for charge) are cited in the literature. These voltage values are obtained using electrophoresis measurements, which are only indirectly related to the actual cell charge. Frequently, these "charge" measurements are made using a turn-key device such as a Zeta-Sizer, which works by using laser light scattering to measure drift velocity of charged particles in an electric field (while suspended in a buffer solution). The directly measured quantity is the velocity v given by:

$$v = \mu E$$

where E is the applied field (typical value: $E \sim 10^{-1}$ V/m), and where μ is the electrophoretic mobility, a derived quantity that depends on the properties of the charge particle. For particles having sizes near those of a cell, one has:

$$\mu = \epsilon_r \epsilon_0 \zeta / \eta$$

(Smoluchowski's equation) where $\epsilon_r$ is the relative permittivity, where η is the viscosity, where $\epsilon_0$ is the permittivity in vacuo, and where ζ is the Zeta potential. For a typical measurement, one has $\zeta \sim 10^{-2}$ to $10^{-1}$ V, $\eta \sim 10^{-3}$ Pas, and $\epsilon_r \sim 80$, which implies $\mu \sim 0.7\text{-}7.0 \times 10^{-8}$ m$^2$s$^{-1}$V$^{-1}$, which in a typical field of $E \sim 10^{-1}$ V/m implies:

$$v = \mu E = (0.7 \times 10^{-8} \text{ m}^2\text{s}^{-1}\text{V}^{-1} \text{ to } 7.0 \times 10^{-8} \text{ m}^2\text{s}^{-1}\text{V}^{-1}) \times (10^{-1} \text{ v/m}) = 0.7 \times 10^{-9} \text{ ms}^{-1} \text{ to } 7.0 \times 10^{-9} \text{ ms}^{-1}$$

Assuming that the particles are small, the electric force F that they experience is:

$$F = E \times q$$

where q is the total charge on the particle. This is balanced by the viscous drag of the suspending medium given by:

$$F = 6\pi \eta R v$$

for a small spherical particle, of radius R, moving at velocity v, which is low enough to prevent turbulence. If one assumes a typical cell radius of $R \sim 10^{-5}$ m and use the typical values for v and η cited above, one has:

$$F \sim 6\pi \eta R v = 6\pi \times 10^{-3} \text{ Pas} \times 10^{-5} \text{ m} \times 0.7\text{-}7.0 \times 10^{-9} \text{ m/s} = 1.3\text{-}13 \times 10^{-16} \text{ N}$$

Inserting this value into F=Eq above, and using the typical value of $E \sim 10^{-1}$ V/m gives:

$$F: (1.3 \times 10^{-16} \text{ N to } 1.3 \times 10^{-15} \text{ N}) \approx 10^{-1} (\text{V/m}) \times q$$

which solves as $q = 1.3 \times 10^{-15}$ to $13 \times 10^{-15}$ coulombs. If one assumes that this charge resides on the surface of the cell, it will produce a normal electric field on the order of 100 V/cm to 1000 V/cm. The inventors estimate that a field in this range will produce an output voltage of 27 to −270 μV in a nanoscale EEC sensor 900 with a 0.5 V forward bias voltage applied between the metal shunt and output current lead. Thus, the surface charge induced bias field at the semiconductor/metal interface 908 should be easily detectable in the voltage response of the EEC sensor.

Moreover, in instances where the Schottky barrier of the EEC nanosensor is detrimentally perturbed by chemical impurities at the semiconductor/metal interface 908, the inventors believe that adding a forward bias voltage to the barrier should alleviate this issue.

Figure 10:
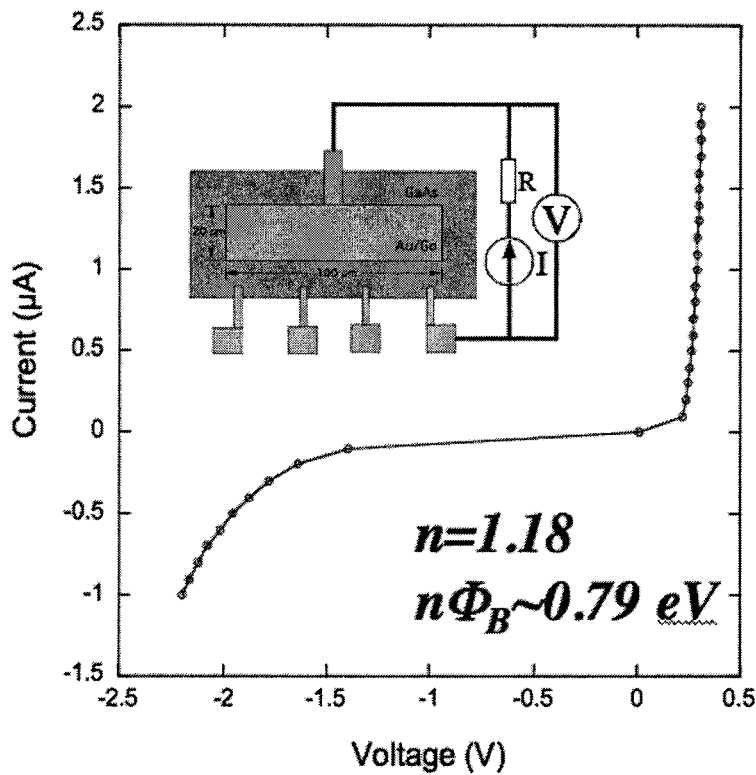
FIG. 10 depicts an I-V curve measured between the shunt and the semiconductor for an exemplary EEC sensor.

FIG. 10 depicts a measured current-voltage plot of a horizontal configuration for an EEC sensor 900 having a Schottky barrier interface between GaAs and In as shown in the inset of FIG. 10. The dimensions of this EEC sensor were 60 μm×30 μm×50 nm, with respect to the x, y, and z axes respectively. From this plot, it can be noted that there is an exponential increase of current with forward bias (positive) voltage in the 0-0.5 V range and that the current is nil in the reverse bias range to about −1.5 V. At higher reverse bias, current leakage results as indicated in FIG. 10.

Figure 11:
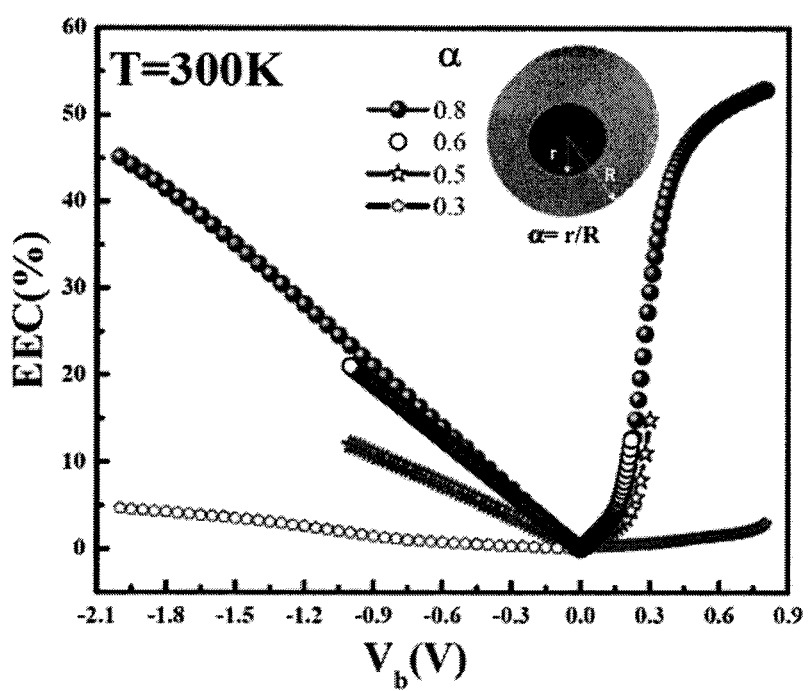
FIG. 11 depicts an EEC measurement for an exemplary EEC sensor.

FIG. 11 depicts a measured EEC characteristic of a circular EEC sensor as shown in the inset of FIG. 11. These EEC measurements were made as a function of the geometric filling factor, α=r/R (see FIG. 11 inset) and of the direct forward and reverse bias on the Schottky barrier for fields in the range of −1050 V/cm to +450 V/cm, as indicated in FIG. 11. It can be noted that the estimates of the field at the surface of a cancer cell due to the known total charge of $\sim 1 \times 10^{-15}$ Coulomb is in the range $10^2\text{-}10^5$ V/cm. In this regard, as a quantitative measure of the EEC effect, one can define the EEC effect as:

$$EEC = 100\% \frac{\lfloor G_{w/field} - G_{n/o\text{-}field} \rfloor}{G_{n/o\text{-}field}}$$

wherein G is the conductance of the EEC sensor, and wherein "with field" means in the presence of the external field that perturbs the EEC sensor (e.g., the field produced by the surface of a cancer cell).

As can be seen in FIG. 11, the EEC depends strongly and increases with filling factor in both the forward and reverse bias directions, reaching values in excess of 50% on saturation in the forward direction. By selectively doping the semiconductor 902 with Si to tune the properties of the Schottky barrier, further improvements to the EEC sensor performance can be expected.

With respect to these nanoscale EXX sensors, a variety of combinations of semiconductor materials, metal shunt materials, and substrate materials can be chosen.

For EMR nanosensors, examples of suitable semiconductor materials include InSb, InAs, and $Hg_{1-x}Cd_xTe$, or any narrow gap semiconductor, and an example of a suitable metal is Au or any good non-magnetic metal. Examples of suitable a substrate material for EMR nanosensors include any highly insulating wide gap semiconductor or insulator, with the preferred material being GaAs both because of its advantageous properties and cost.

For EPC and EAC nanosensors, examples of suitable semiconductor materials include GaAs, InAs or other III-V semiconductors, and examples of suitable metals include Au or any other high conductivity metal. With respect to a substrate material for EPC/EAC nanosensors, the choice of substrate material may vary based on the type of perturbation for the sensor. For example, one can select a "stiff" substrate such as GaAs to detect high frequency, large amplitude acoustic signals, whereas GaSb would be a more desirable choice for low amplitude, low frequency signals. Signal selectivity can also be tuned through judicious design of the substrate's dimensional and geometric properties—for example, a long, thin and narrow substrate would also be linearly responsive to weak acoustic perturbations while a thick substrate would be more linearly responsive to stronger acoustic perturbations. In situations where both the substrate and semiconductor film are made of GaAs materials, the GaAs used in the semiconductor film should have a different impurity concentration than the GaAs used in the substrate.

For EOC nanosensors, examples of suitable semiconductor materials include GaAs, InSb, and other direct gap semiconductors, and examples of suitable metals include In or any high conductivity metal. Examples of a suitable substrate material include GaAs and other high resistance materials. Once again, in situations where both the substrate and semiconductor film are made of GaAs materials, the GaAs used in the semiconductor film should have a different impurity concentration than the GaAs used in the substrate.

For EEC nanosensors, examples of suitable semiconductor materials include GaAs, and other doped semiconductors, and examples of suitable metals include Au or any other high conductivity metal. Examples of a suitable substrate material include GaAs or any suitably insulating substrate material. Once again, in situations where both the substrate and semiconductor film are made of GaAs materials, the GaAs used in the semiconductor film should have a different impurity concentration than the GaAs used in the substrate.

With respect to providing a current flow to the EXX nanosensors, a suitable biasing current is preferably in a microamp or milliamp range depending upon the application and the actual type of EXX sensor.

Figure 12A:
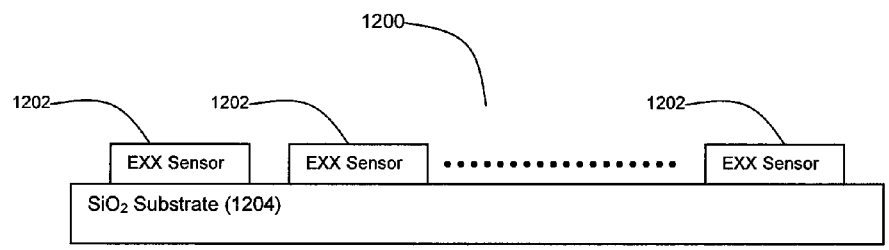
FIG. 12($a$) is a cross-sectional view of an exemplary array of EXX sensors.
Figure 12B:
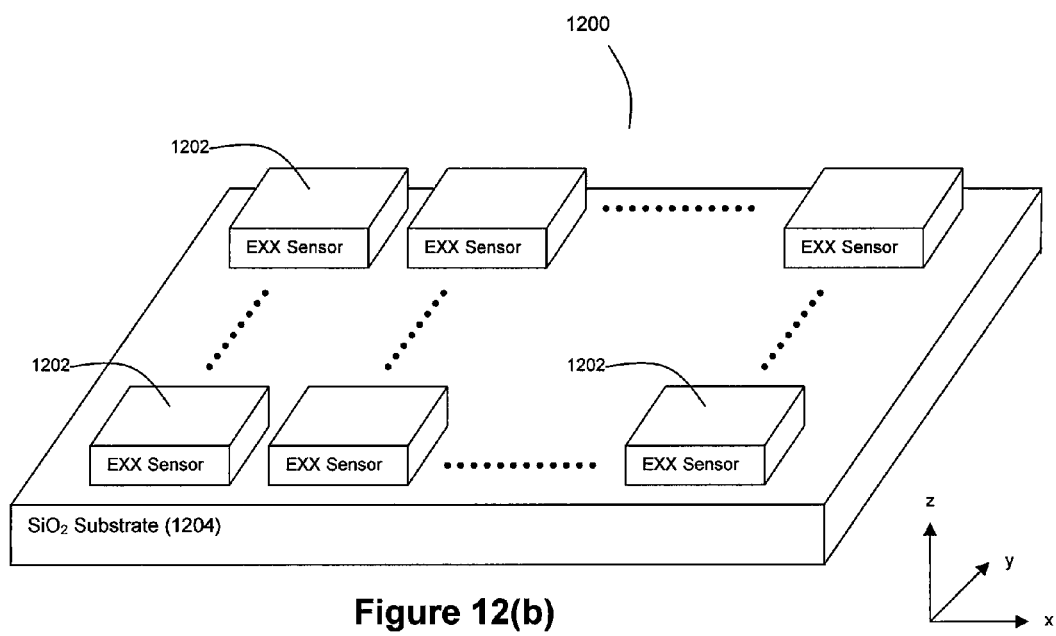
Figure 13:
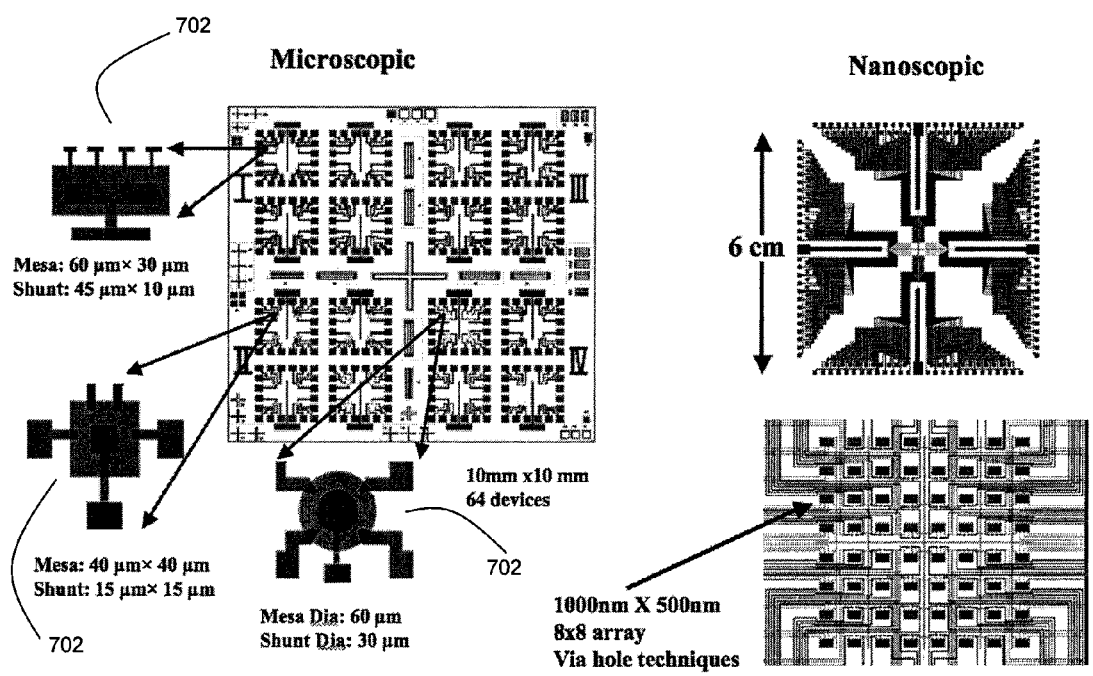
FIG. 13 depicts schematic diagrams for exemplary multi-EXX sensor arrays showing various pixel geometries.

The nanosensors described above in connection with FIGS. 1-9 can be combined to create an N×M array 1200 of multiple nanoscale EXX sensors 1202 as shown in FIGS. 12(a) and 12(b). The values of N and M can be chosen by practitioners of the present invention as a design choice based on their intended use of the nanoscale EXX sensors (e.g., 4×4, 16×16, 2×20, 64×64, etc. with upper values only bounded by manufacturing capabilities). For example, the inventors contemplate that nanosensor matrix dimensions judging from current digital display technologies can also be 640×480, 800×600, 1024×768, 1600×1200, 2048×1536, and 3200×2400. These nanoscale EXX sensors 1202 can be deposited on an array substrate 1204 such as an $SiO_2$ substrate. A preferred thickness for substrate 1204 is approximately 400 μm, although other thicknesses can be used. It should be noted that the voltage and current leads of the individual nanoscale EXX sensors are not shown in FIGS. 12(a) and (b) for ease of illustration. It should also be noted that a via design for row/column pin-out addressing from the matrix of nanosensors 1202 in the array 1200 can be used, particularly for arrays having large numbers of nanosensors (see FIG. 13). For the array structures shown in FIG. 13, each of the 4-leads for the EXX sensors 1202 can be individually addressable, thereby yielding $4n^2$ pin-outs for an n×n array. Furthermore, these leads can be selectively combined to yield a reduction to $3n+1$ pin-outs for an n×n array.

It should also be noted that in instances where the individual EXX sensors are designed to have a substrate 106 of the same material as substrate 1204, then the EXX sensor 1202 that is located on array 1200 will not need to include substrate 106 as the material of substrate 1204 can then serve as the appropriate substrate. However, if the substrate materials are dissimilar, then the individual EXX sensors 1202 will preferably include their own substrate 106 (e.g., when the EXX sensor 1202 has a GaAs substrate 106 while the array 1200 has an $SiO_2$ substrate 1204). Preferably, the array 1200 exhibits tight spacing between EXX sensors 1202. For example, a spacing value that falls within a range of approximately 50 nm to approximately 1000 nm can be used.

The selection of EXX sensor type(s) and distribution of EXX sensor type(s) over the array 1200 can be highly variable. For example, the array 1200 can include only nanoscale EXX sensors 1202 of a single type (e.g., an array of only EAC sensors, an array of only EOC sensors, an array of only EEC sensors, etc.) Also, the array 1200 can include a plurality of different types of nanoscale EXX sensors, such as any combination of nanoscale EMR/EPC/EAC/EOC/EEC sensors 1202. Integrating multiple different types of EXX nanosensors in an array (such as EAC/EOC/EEC nanosensors) will provide for a screening system capable of performing HCS for prospective interrogation of cells based on the outcome of charge and fluorescent imaging, like LSC. However, the resolution of the acoustic subsystem will be equal to or greater than that obtained from optical microscopy, and moreover will represent volumetric data (i.e., not be limited to a single focal plane at a time), as the time axis of the digitized ultrasound waveforms contains information that can be mapped to distance into the cell being imaged via the dispersion relationship directly analogous to imaging organ structures with currently available clinical ultrasound systems. This type of instrumentation would offer several advantages not available in current cytometry/microscopy instruments such as simultaneous acquisition of volumetric data based on nanoscale acoustic microscopy, higher resolution than current optical microscopy without necessarily requiring expensive high intensity light sources, high precision and resolution surface charge measurements without the complications and ambiguities inherent in electrophoretic techniques, and high resolution, low noise fluorescent imaging.

Figure 14A:
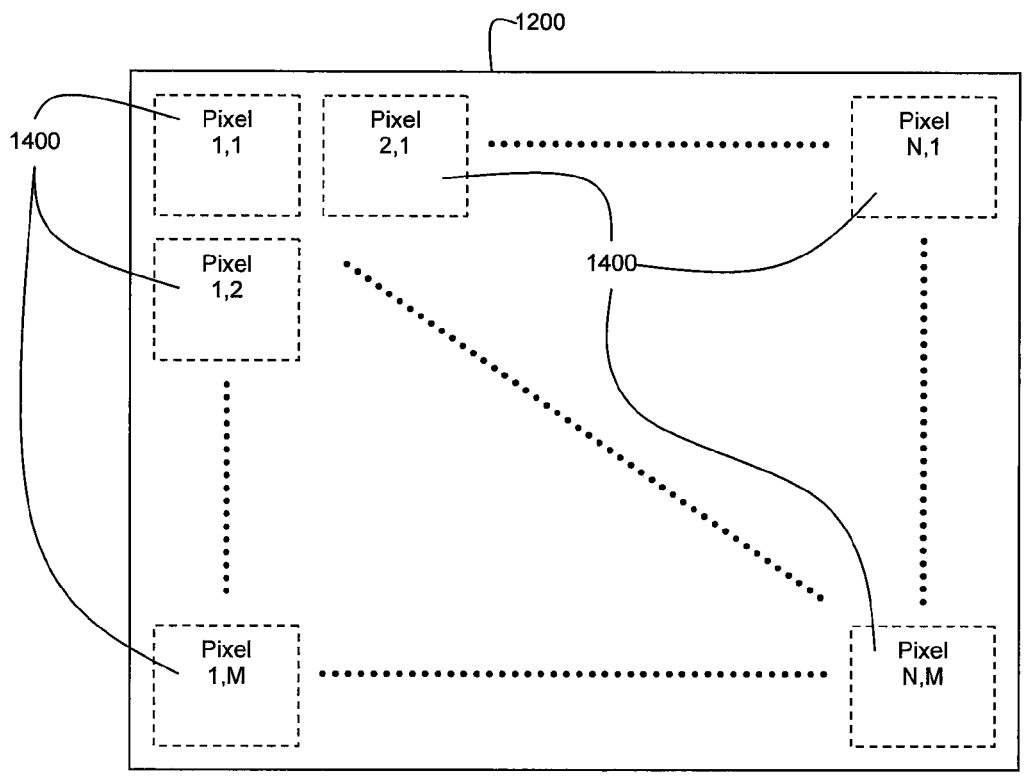
FIG. 14($a$) is a top view of an exemplary array whose nanosensors are organized as a plurality of pixels.
Figure 14B:
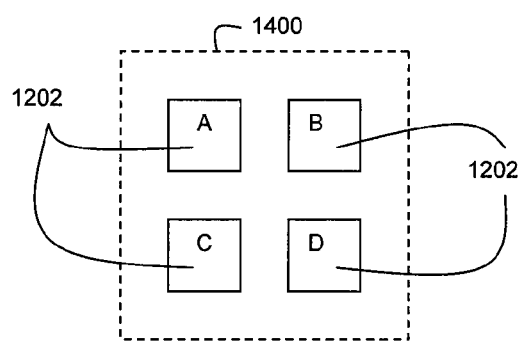

It should also be noted that the array 1200 can be thought of as being subdivided into a plurality of pixels 1400, as shown in FIG. 14(a). Each pixel 1400 can comprise one or more nanosensors 1202. For example, as shown in FIG. 14(b), a pixel 1400 can comprise a plurality of different types of nanosensors 1202, such as 4 nanosensors of types "A", "B", "C", and "D" (wherein type "A" could correspond to an EOC nanosensor, wherein type "B" could correspond to an EPC nanosensor, wherein type "C" could correspond to an EEC nanosensor, and wherein type "D" could correspond to an EMR nanosensor). Such groups of different types of nanosensors within a pixel 1400 can be helpful for increasing the sensitivity of the array 1200 by using signal averaging techniques on the voltage responses of the nanosensors.

Figure 15A:
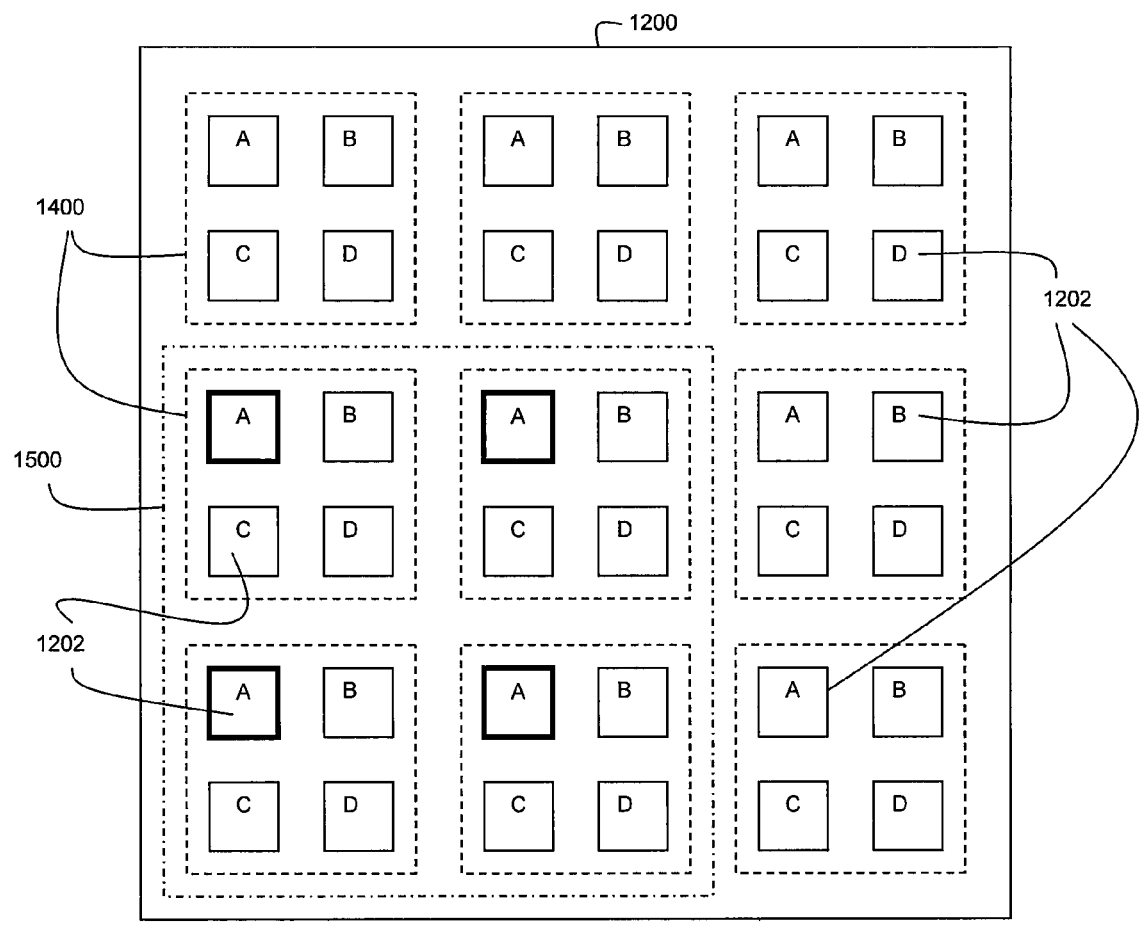
FIGS. 15($a$) and ($b$) depict exemplary arrays that show how different nanosensors can be grouped into composite pixels.

Similarly, it should be noted that pixels 1400 or portions thereof can be grouped with other pixels 1400 or portions thereof to form composite pixels. For example, FIG. 15(a) depicts a composite pixel 1500 formed from a grouping of 4 pixels 1400 of the arrangement shown in FIG. 14(b). Furthermore, the composite pixel 1500 can be formed of only a single type of nanosensors (e.g. only the "A" type nanosensors within those four pixels 1400, as shown by the boldface notation in FIG. 15(a)). Once again, such arrangements of composite pixels can be helpful for increasing sensitivity through the use of signal averaging techniques.

Figure 15B:
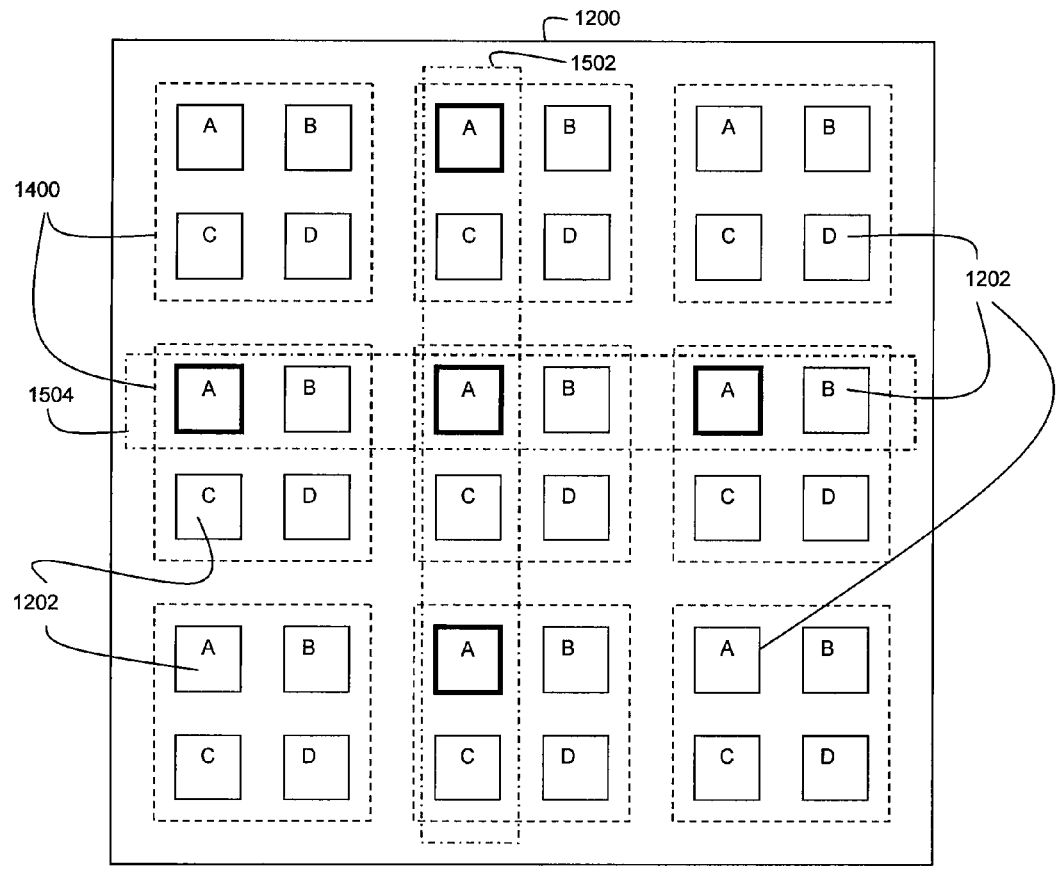

FIG. 15(b) depicts an example of a composite pixel 1502 that is formed from a plurality of nanosensors of the same type that are arranged in a straight line and has a length of a plurality of pixels 1400 (e.g., the "A" type nanosensors shown in boldface within composite pixel 1502). FIG. 15(b) also depicts an example of a composite pixel 1504 that is formed from a plurality of nanosensors of the same type that are arranged in a straight line orthogonal to composite pixel 1502 and has a length of a plurality of pixels 1400. Composite pixels arranged such as composite pixels 1502 and 1504 can be useful for phase-type imaging of optical signals, polarizing deflected light, or detecting different acoustical modes (e.g., shear, transverse, various plate modes) depending on the type of nanosensor employed.

As an object such as one or more cells is placed into contact with the array 1200 on the exposed surfaces of the EXX sensors 1202, and as the EXX sensors 1202 of the array are perturbed, the voltage responses of the various EXX sensors 1202 can be measured, digitized, stored, and processed by receiver electronics including a signal processor (not shown). The collection of voltage responses can in turn be selectively pixelized based on the spatial relationship among the EXX sensors to generate an image of the object that is indicative of one or more characteristics of the object. Both single-modality images and multi-modal parameterized images can be generated by registering and combining the output from different types of nanosensors. Because of the nanoscale of the array's EXX sensors, the resultant images would also exhibit a resolution that is nanoscale. Furthermore, each nanoscale EXX sensor 1202 can be independently addressable by the receiver electronics to permit an increased data acquisition rate (imaging frames of a given area of an object per unit time). Also, it should be noted that to enhance the ability of cells to grow and adhere to the array surface, the exposed surface of the array on which the one or more cells contact the array can be coated with a protein such as fibronectin, vitronectin, collagen, or a protein-mimetic such as poly-l-lysine or silane.

For example, with an array 1200 comprised of multiple EAC and EEC sensors 1202, after a cell is placed on that array, the array can be perturbed with an acoustic wave to obtain voltage responses from the EAC sensors from which an ultrasonic image of the cell having nanoscale resolution can be generated. At the same time, the EEC sensors on the array 1202 can be perturbed with a surface charge from the cell itself to produce voltage responses from the EEC sensors from which an image having nanoscale resolution and representative of the spatial distribution of electric charge over the cell can be generated. Further, still, because the surface charge from the cell is not likely to perturb the EAC sensors and because the acoustic wave is not likely to perturb the EEC sensors, cross-talk between the EEC and EAC sensors can be minimized, and images of multiple characteristics of the cell can be simultaneously generated.

However, it should be noted that in instances where the array 1200 includes both EAC/EPC sensors and EOC sensors, cross-talk can occur where the light perturbation causes an undesired voltage response in the EAC sensor and the acoustic perturbation causes an undesired voltage response in the EOC sensor. To reduce the effects of such cross-talk, one can selectively perturb the EAC sensors at a different time than the EOC sensors with sequentially applied perturbations and selective interrogation of the nanosensors based on which perturbation has been applied. In instances where the cell itself is the source of the light perturbation (presumably not a spontaneous light emission by the cell but rather a light emission following exposure to an external optical field), cross-talk can be reduced when there is a phosphorescent component present within the cell. In such a case, signal processing techniques (lock-in amp, digital lock-in, pulse gating, time correlation, etc.) can be used to distinguish EAC and EOC signals. For EOC in the cases of absorption and reflectance the response of the cell will be essentially instantaneous, e.g. the absorption and reflection signals will have essentially the same profile as the incident light signal with essentially no phase delay on the time scales of relevance here. So temporal separation of either absorption or reflection EOC from EPC should not be problematic. In the case of fluorescence, the EOC signal will depend on the fluoroescence lifetime of the cell. If this is in the sub microsecond range or shorter, the fluorescence signal can be handled in the same way as absorption and transmission EOC. If it is of order a millisecond or longer, then an (essentially DC) EOC baseline shift can be added to the EPC signal but the signal above the base line should still be easily discernable. The corrollary is applicable for detection of an EPC signal in the presence of a long lived fluorescence, but by gating the detection system to coincide with the shorter time acoustic signal the baseline shift can be rejected. There are also hardware methods to accomplish signal selection. By fabricating a substrate with thick and thin regions and depositing the EOC sensors on the thick regions and the EPC sensors on thin ones, the EOC regions can be made impervious to acoustic signals, whatever their temporal properties. Similarly, by depositing a thin but optically opaque surface film on only the EPC sensors, they can be made impervious to any optical signals regardless of their temporal properties.

The source of the pertubation(s) for the EXX sensors 1202 can be one or more external perturbation sources as explained above, the object itself (particularly for EOC and EEC nanosensors), or a perturbation source that is integral to the array. For example, a laser source such as a near-field scanning optical microscope (NSOM) can use SAFT techniques to spatially localize a photon field to a small size (on the order of 1 micron or less and less than the spacing between EXX sensors on the array) that can be scanned/driven in X and Y directions across the array by the piezoelectric X and Y motion controls of a scanning tunneling microscope (STM) to which the NSOM has been attached/adapted. The STM could be used to perturb any EAC nanosensors while the NSOM could be used to perturb any EOC nanosensors. The NSOM would guide light from the appropriate laser through a submicron-sized aperture at the end of a tapered and metallized optical fiber. The near field method can provide photon fields with a lateral localization as small as 500 nm in the visible region. Further still, a spatially localized field for perturbing EEC nanosensors could be obtained by mounting a tapered metallic tip to the STM scanner and applying a known voltage between the tip and a metallized back surface on the substrate 1204. For both the laser perturbation and the electric field perturbation, the spatial resolution of the applied field would depend on its maintaining close proximity to the surface of the sensor array. Such proximity can be maintained by feedback control of the STM's Z-motion via a signal from the STM (guiding) tip.

It is also worth noting each of the array's EXX sensors can receive its own biasing current flow such that not all of the array's EXX sensors will receive the same current flow. For example, EXX sensors 1-10 of an array may receive current A while EXX sensors 11-20 of that array may receive current B.

As a further example, 20 different currents could also be delivered to the array's 20 EXX sensors.

Figure 16A:
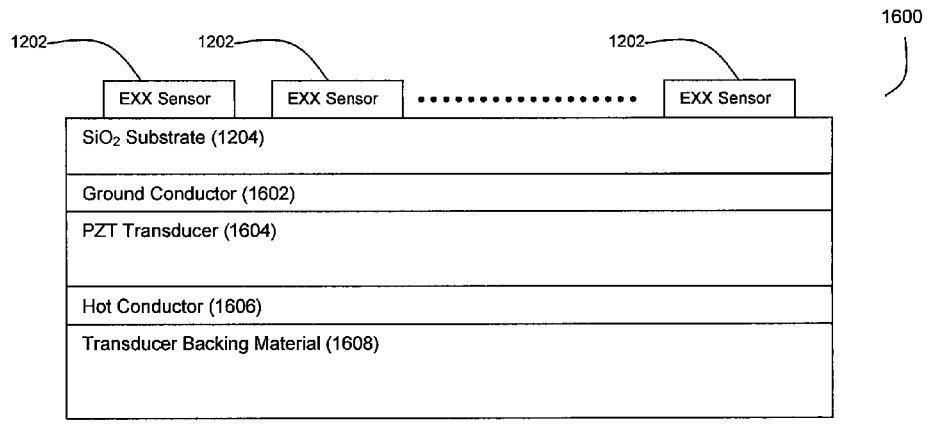
FIG. 16($a$) is a cross-sectional view of an exemplary array of EXX sensors having an integral macro-scale PZT transducer.
Figure 16B:
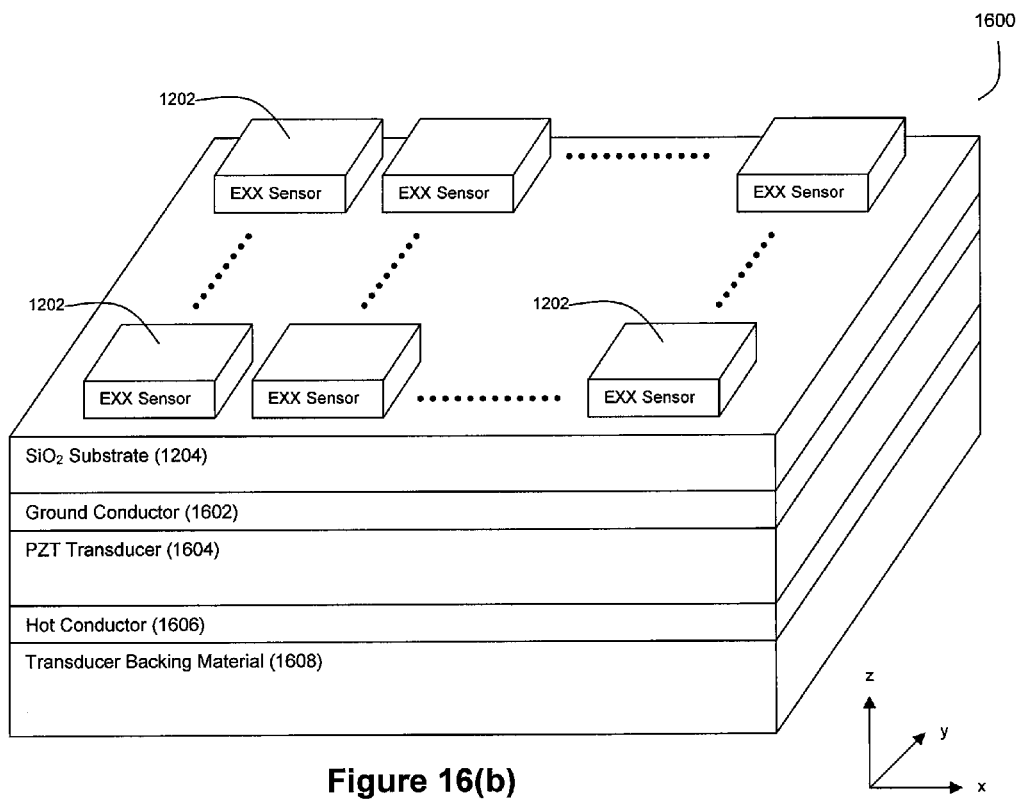

FIGS. 16(a) and (b) illustrate another array embodiment for the present invention wherein a perturbation source is integral to the array 1600. The array 1600 includes an integral PZT transducer 1604 that serves to generate the acoustic wave for perturbing the array's EAC/EPC nanosensors 1202. As with the array 1200, the voltage and current leads of the individual nanoscale EXX sensors 1202 are not shown in FIGS. 16(a) and (b) for ease of illustration. However, it should be noted that ground-signal-ground (GSG) wiring geometries for electrical traces deposited on substrate 1204 to the nanosensor leads can be employed to improve characteristics in the UHF and SHF ranges of signal frequencies. With array 1600, the EXX sensors 1202 and substrate 1204 can be arranged as explained above in connection with FIGS. 12(a) and (b). However, due to the presence of the PZT transducer 1604, it is preferred that at least some of the nanoscale EXX sensors 1202 are EPC/EAC sensors. The array 1600 also preferably includes a transducer backing material 1608 that lies in a plane substantially parallel to the plane of substrate 1204. A material and thickness for the backing material 1608 is preferably selected to have an acoustic impedance that is similarly-matched to the acoustic impedance of the piezoelectric thin-film transducer 1604 and lossy enough (to attenuate the acoustic wave launched into the backing material) to minimize undesired multiple reverberation resonance effects and to "spoil the Q" of the thin-film 1604 to effectively broaden the useful frequency bandwidth of the device (corresponding to shorter time pulses and greater axial resolution). An example of a backing material 1608 could be an epoxy-resin with ground Tungsten particles. However, it should be noted that other backing materials may be used as explained above. Furthermore, as the broadband transducer gets into the GHz range (rather than the MHz range), the inventors herein believe that the choice of backing materials 1608 may be less impactful on performance.

Disposed between the substrate 1204 and the backing material 1608 is a macroscale piezoelectric transducer 1604 in contact with a ground conductor 1602 and a hot conductor 1606. The macroscale piezoelectric transducer 1604 also preferably lies in a plane that is substantially parallel to the plane of the substrate 1204. By driving the piezoelectric transducer 1604 with a current flow through conductors 1602 and 1606, the piezoelectric transducer emits a broadband acoustic plane wave whose plane is substantially parallel to the plane of substrate 1204 and whose direction of propagation is substantially normal to the plane of substrate 1204 (and by derivation in plane with the plane of the semiconductor/metal interfaces 108 of the EPC/EAC nanosensors of the array). This broadband acoustic plane wave serves as the perturbation for the EPC/EAC nanosensors. The piezoelectric transducer 1604 can be formed from a thin-film piezoelectric transducer material, such as thin-film poly-crystalline or single crystal of perovskite ceramic materials (e.g., PZT: Lead Zirconate Titanate, and doped-derivatives such as PNZT: Niobium-doped PZT, PLZT: Lanthanum-doped PZT, PMN-ZT: magnesium niobate-doped PZT, etc.), or polymer materials (e.g., PVDF: Polyvinylidene difluoride) and exhibit a thickness between approximately 20 nm and approximately 2000 nm to tune the frequency response to a desired range. However, it should be noted that other materials and thicknesses can be used. The frequency of the broadband acoustic plane wave can be in the GHz range (e.g., approximately 1-5 GHz), although other frequency values can be used.

The broadband plane wave produced by the macroscale PZT transducer 1604 serves to improve the quality of images reconstructed from backscattered ultrasound, and the array 1600 permits insonification of an object being imaged at pressure levels that would be difficult to obtain using a nanoscaled acoustic transmitter. Moreover, by separating the transmit and receive elements (transducer 1604 and nanosensors 1202 respectively), the receiving electronics (not shown) can be greatly simplified to permit higher drive levels on transmit and to improve both SNR and bandwidth aspects of signal receipt. Furthermore, by integrating both the transmit and receive elements into a single array, the need for external acoustic perturbation sources such as expensive SAMs can be avoided.

Figure 17:
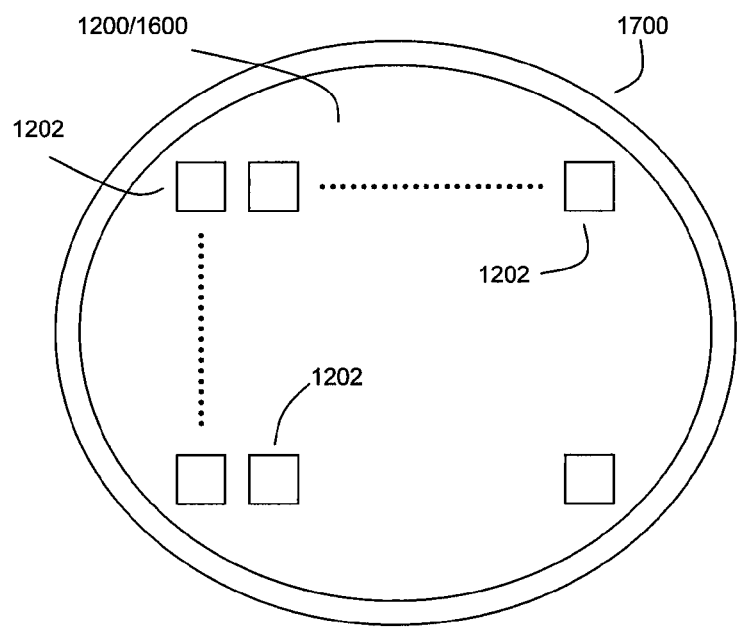
FIG. 17 is a top view of a cell culture dish having an array of nanoscale EXX sensors incorporated therein.

The integrated array 1600 or the array 1200 can be mass produced to provide inexpensive (even disposable) imaging devices that could be incorporated into the bottoms of cell culture dishes 1700 (see FIG. 17), thereby providing the ability to acoustically image either large numbers of or single cells and to continuously provide data that facilitates monitoring of the safety and efficacy of therapeutic agents intended for treatment of diseases such as cancer, heart disease, inflammatory conditions, etc.

Figure 18:
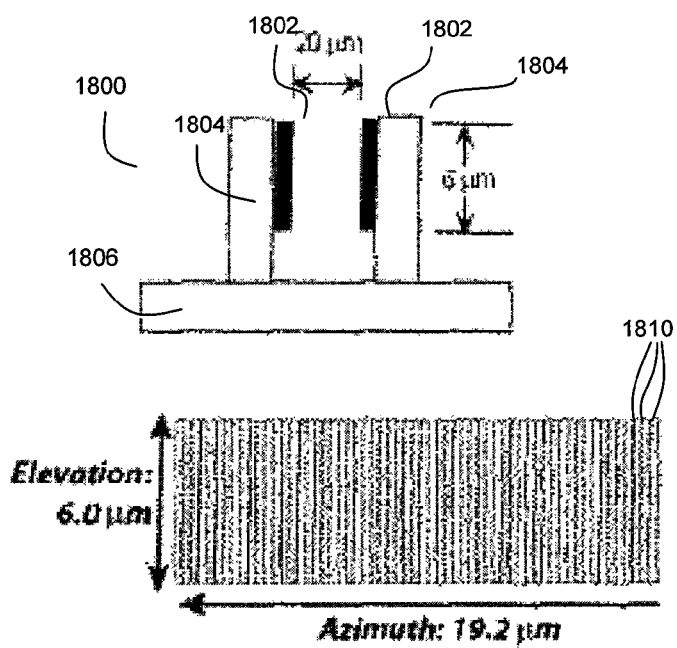
FIG. 18 depicts an exemplary pitch-catch linear array of multiple PZT transducers.

FIG. 18 illustrates another embodiment of an imaging array in accordance with the present invention. FIG. 18 depicts a multi-element pitch-catch array 1800. The array 1800 comprises 64 pairs of rectangular piezoelectric (e.g., PZT or other piezoelectric materials such as described above) elements 1810 that are spaced evenly in a linear configuration of opposing pairs 1802 that are 20 µm apart. Base 1806 and supports 1804 hold the pairs 1802 of PZT elements 1810 in opposition to each other. Driving electronics (not shown) for delivering power to the PZT elements will also be included in the array 1800. Exemplary dimensions for the piezoelectric elements are 6.0 µm high, 300 nm thick, 250 nm wide, and with a 50 nm spacing between elements (for a 300 nm element pitch and an overall azimuth of 19.2 µm for all 64 elements). However, other dimensions can be used, wherein Sol Gel deposition can be used as a technique to fabricate nanoscale PZT elements.

The 64 PZT elements 1810 (that are shown in a front view in the bottom portion of FIG. 18) are configured to generate ultrasonic pulses that will propagate across the 20 µm gap to their opposing partners, which will function as receivers. In a pulse/echo mode, the 64 PZT elements on the opposing side of the array will act as reflectors. An object to be imaged by array 1800 can be placed between the opposing pairs 1802 and ultrasound pulses can be used to generate ultrasound data from which ultrasound images of the object can be reconstructed.

Furthermore, an N×M (e.g., 16×16) array like the one shown in FIGS. 12(a) and (b) can be made of these PZT elements 1810, fabricated on the nanoscale, for use in the generation of ultrasound images. As with the arrays 1200 and 1600, such an array can be used to generate ultra high resolution images of a cancer cell that is grown on the array surface. Acoustic images of such a cancer cell can be made with ultrasound at frequencies such as 2.7 GHz or 5.2 GHz using SAFT techniques. To improve such an array's SNR, the pulse-repetition frequency of the ultrasound pulses may be increased, and/or signal averaging techniques can be used. Because the transmit frequency for the preferred ultrasound pulses is high (preferably in the GHz range; thereby implying short pulse lengths) and because the round trip distance would be short, the inventors herein envision that signal averaging for such arrays will not face the usual problems that limit signal averaging's utility to conventional ultrasonics. It should also be noted that the arrays 1200 and 1600 described above could incorporate nanoscale PZT elements 1810 in combination with the individual EXX sensors 1202 described above.

Figure 19:
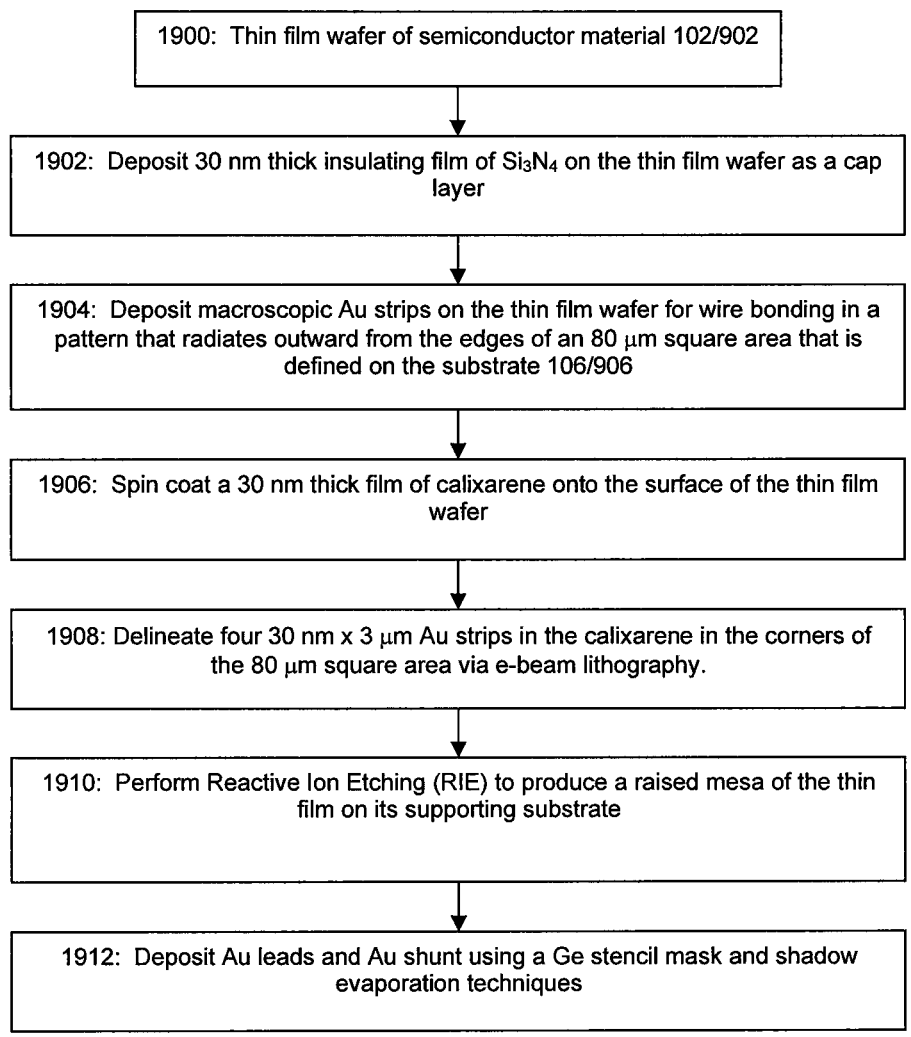
FIG. 19 is a flowchart describing an exemplary method for fabricating a nanoscale EXX sensor.

FIG. 19 depicts a methodology for fabricating nanoscale EXX sensors using a multi-step electron beam (e-beam) lithography process At step 1900, a thin film wafer of semiconductor material 102/902 is provided. Next at step 1902, a 30 nm thick insulating film of $Si_3N_4$ (added to prevent shorting between the leads and the shunt) is deposited on the thin film wafer as a cap layer. At step 1904, macroscopic Au strips for wire bonding are deposited on the cap layer in a pattern that radiates outward from the edges of an 80 µm square area that is defined on the substrate 106/906. Next, at step 1906, a 30 nm thick calixarene film is spin coated onto the surface of the thin film wafer. At step 1908, four 30 nm×3 µm Au strips will be delineated in the calixarene in the corners of the 80 µm square area by e-beam lithography. This calixarene pattern and the macroscopic Au strips will serve as a mark for reactive ion etching (RIE) of the $Si_3N_4$ layer using conventional methods (step 1910). This RIE process (step 1910) produces a raised mesa of the thin film on its supporting substrate. For InSb films, an appropriate etchant is a $CH_4+H_2$ mixture. The residual $Si_3N_4$ and Au strips serve as an RIE mask. Then, at step 1912, Au leads and an Au shunt will be deposited using a Ge stencil mask and a shadow evaporation technique. The inventors believe that such fabrication will result in EXX nanosensors with a volumetric resolution of 35 nm (the voltage probe spacing set by the limits of suspended mask e-beam lithography)×30 nm (the width of the mesa set by RIE etching properties and the resolution of calixarene resist patterns)× 25-250 nm (the thickness of the thin film material, along the x-, y-, and z-axes respectively. See Solin et al., *Room temperature extraordinary magnetoresistance of non-magnetic narrow-gap semiconductor/metal composites: Application to read-head sensors for ultra high density magnetic recording*, IEEE Trans Mag., 2002; 38, pp. 89-94; Pashldn et al., *Room-temperature Al single-electron transistor made by electron-beam lithography*, Applied Physics Letters, 2000; 76, p. 2256; M. Sugawara, *Plasma Etching, New York; Oxford*, 1998, the entire disclosures of each of which are incorporated by reference herein. As would be understood by a person having ordinary skill in the art, this technique can be applied to the fabrication of not only EPC, EAC, EOC, EMR, and EOC nanosensors but also EEC nanosensors (although the fabrication of the EEC nanosensors may be less demanding because of the architectural difference therebetween).

To minimize leakage current through the floor of the mesa, an insulating $Al_2O_3$ barrier can be first prepared by depositing and subsequently oxidizing a layer of Al to within 50 nm of the mesa sidewall. An alignment accuracy of about +/−10 nm normal to the mesa sidewall is desired.

Furthermore, when fabricating an array 1200 or 1000, it is preferred that the EXX nanosensors 1202 be designed and fabricated together as an array rather than individually fabricating each EXX nanosensor 1202 and then aggregating the individual EXX nanosensors 1202 into an array.

Also, when fabricating an array of nanoscale EXX sensors, a substrate 1204 thinning process can be used to optimize the array's performance, although this thinning is preferably achieved using a feedback-controlled process that thins the substrate at increasingly slower and controllable rates to avoid a punch through of the EXX sensors through the substrate. Further still, when fabricating such arrays of interdigitated nanosensors, several additional mask steps can be used in the suspended mask e-beam lithography process.

The SAFTs referenced above can be implemented using conventional SAFTs or several variants thereof, wherein the variants of the conventional SAFT algorithm reduce the number of array elements required and offer improvements in SNR. These variants include multielement-subaperture SAFT (see Gammelmark et al., "*Multielement synthetic transmit apertum imaging using temporal encoding*", IEEE Transactions on Medical Imaging, 2003; 22, pp. 552-63, the entire disclosure of which is incorporated herein by reference), which has been shown to achieve higher electronic signal to noise ratio and better contrast resolution than the conventional synthetic aperture focusing techniques. Another SAFT approach is based on sparse array SAFT which offers the advantage of a reduction in the number of array elements (obtained at the price of lower transmitted and received signal). These drawbacks can be minimized by increasing the power delivered to each transmit element and by using multiple transmit elements for each transmit pulse. Another SAFT option is to use a combination of B-mode and SAFT that has been shown to improve lateral resolution beyond the focus of the transducer and by using apodization to lower the sidelobes, but only at the expense of lateral resolution, as with classical synthetic aperture imaging. Results obtained by this technique show that, for a 15 MHz focused transducer, the 6-dB beamwidths at 3, 5, and 7 mm beyond the focus are 189 µm, 184 µm, and 215 µm, respectively. For images made by scanning a 0.12 mm wire, SNR is 38.6 dB when the wire is at the focus, and it is 32.8 dB, 35.3 dB and 38.1 dB after synthetic aperture processing when the wire is 3, 5, and 7 mm beyond the focus, respectively. At 1-2 GHz, these beamwidths and SNRs imply resolution would scale down to the nanometer range.

Figure 20:
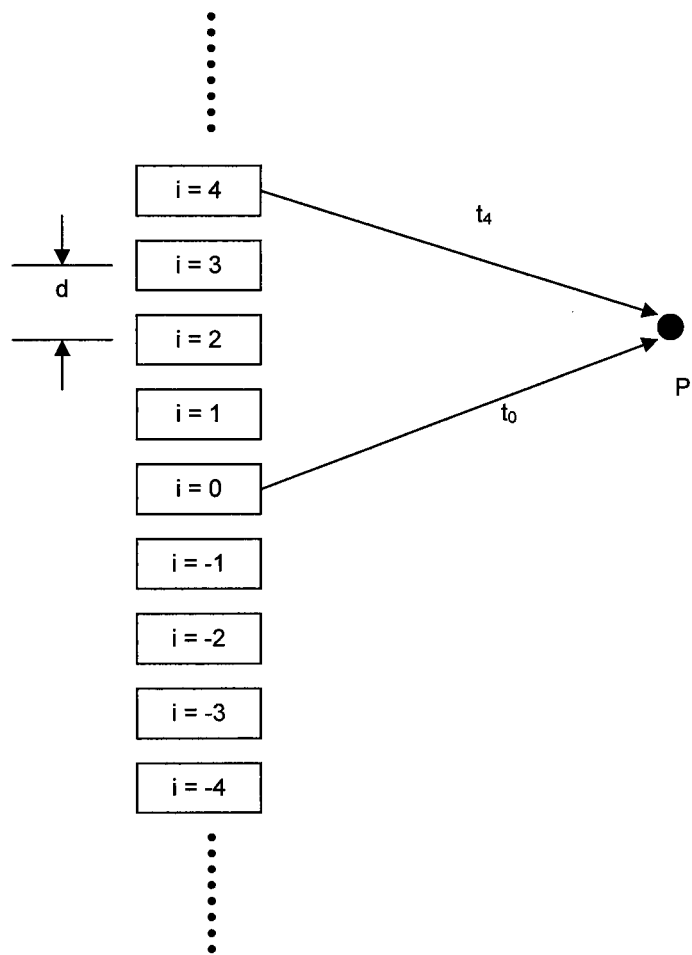
FIG. 20 indicates a synthetic aperture focusing technique applied to a plurality of transmit array elements.

FIG. 20 shows an approach to synthetic aperture imaging that follows Frazier's description. FIG. 20 depicts an array of elements labeled by the index i. In order to simplify the description, only the receive side of the imaging problem where each element is fired simultaneously will be considered. It is desired to process the backscattered signals $S_i(t)$ measured at each array element so that those signals are effectively focused at the point P. This may be achieved by appropriately delaying various signals from the array elements and summing them ("delay-and-sum" beam forming). The field from the array will be focused at the point P if all pulses from the array elements arrive there simultaneously. This can be effected in post-processing if one shifts each backscattered pulse by $$\Delta t_i = 2z/c(1-\sqrt{1+(id/z)})$$

and then summing each of the received waveforms according to:

$$A(t)=\Sigma w_i(P)S_i(t-\Delta t_i)$$

where the $w_i(P)$ terms are weights assigned to each element and are functions of the chosen focal point P and also array element transmit properties that affect the field it transmits. These weights are used to achieve aperture apodization, which is necessary to obtain increased resolution. The inventors have obtained satisfactory results using a unit rectangle function whose width is determined by the transducer used to acquire raw data. See Bracewell, R N, *The Fourier Transform and its Applications*, New York, McGraw-Hill, 1978, the entire disclosure of which is incorporated by reference herein. For applications where higher resolution is desired such as with the nanosensors described herein, other apodizations such those described by Frazier can be used.

While the present invention has been described above in relation to its preferred embodiment, various modifications may be made thereto that still fall within the invention's scope. Such modifications to the invention will be recognizable upon review of the teachings herein. For example, the nanosensor embodiments described herein have been described as having a generally rectangular plate shape. It should be noted that other geometries could be used for the nanosensors. For example, a circular semiconductor material with an embedded concentric metallic shunt. Also, it should be noted that the inventors envision that the nanoscale EXX sensors and/or arrays of such nanoscale EXX sensors can be implanted into a patient's body (such as within a patient's vasculature) for imaging internal bodily conditions of the patient. These sensors or arrays could be implanted in much that same way that subcutaneous pumps, or cardiac pacemakers and defibrillators, or the routes for any prosthetic device are implanted. The inventors contemplate that delivery and deployment via intravascular catheters would be used. Such nanosensors and arrays can be configured with a telemetric output, such as by transmitters incorporated into the arrays that produce signals (e.g. radio signals) that can be monitored remotely with appropriate receivers, as it the case with implanted pacemakers, to provide in vivo ultra high resolution imaging of internal body conditions and processes or they can include on-board local memory in which the voltage responses can be stored for subsequent analysis upon retrieval of the array. For biasing currents, the nanosensors or arrays can be configured with their own on board energy sources.

Further still, the nanosensors and arrays of the present invention may also be used for other non-medical applications, including but not limited to real-time in-process monitoring of any nanoscale events detectable by the sensors and incorporation into field sensors for environmental monitoring. For example, the inventors envision that nanoscale EOC sensors can be useful as position sensitive detectors and as photosensors and that nanoscale EEC sensors can be useful for pixel monitoring in flat panel displays.

Accordingly, the full scope of the present invention is to be defined solely by the appended claims and their legal equivalents.

What is claimed is:

1. An apparatus for sensing a characteristic of an object, the apparatus comprising:
    a planar semiconductor material, the semiconductor material comprising a planar surface; and
    a metal shunt located on the planar surface of the semiconductor material, wherein the metal shunt covers a portion of the planar surface of the semiconductor material, thereby defining a planar semiconductor/metal interface;
    wherein the semiconductor/metal interface is configured to exhibit a change in resistance thereof in response to the semiconductor/metal interface being perturbed by an electric charge perturbation, the change in resistance being indicative of the characteristic of an object that is in proximity to the apparatus.

2. The apparatus of claim 1 further comprising:
    at least two current leads in contact with the semiconductor material for delivering a predetermined current flow to the semiconductor material; and
    at least two voltage leads in contact with the semiconductor material for producing a measurable voltage in response to the perturbation, the voltage being indicative of the characteristic of the object.

3. The apparatus of claim 2 wherein the semiconductor material comprises a semiconductor film having a thickness of in a range of approximately 25 nm to approximately 2000 nm.

4. The apparatus of claim 3 wherein the metal shunt has a thickness in a range of approximately 25 nm to approximately 2000 nm.

5. The apparatus of claim 4 wherein the semiconductor film has a length in a range of approximately 25 nm to approximately 500 nm and a width in a range of approximately 25 nm to approximately 500 nm.

6. The apparatus of claim 5 further comprising a substrate, wherein the semiconductor film is disposed between the substrate and the metal shunt.

7. The apparatus of claim 5 wherein the semiconductor/metal interface is substantially perpendicular to a direction of the perturbation.

8. The apparatus of claim 5 wherein the semiconductor film comprises GaAs, and wherein the metal shunt comprises Au.

9. The apparatus of claim 5 further comprising the object in contact with the apparatus, wherein the object comprises at least one living cell, and wherein an electric charge produced by the at least one living cell serves as the perturbation for producing the voltage.

10. The apparatus of claim 2 further comprising the object in contact with the apparatus, wherein the object comprises at least one living cell, and wherein an electric charge produced by the at least one living cell serves as the perturbation for producing the voltage.

11. A method of generating an image of at least one cell, the method comprising:
    providing a predetermined current flow to a plurality of EEC sensors that are in proximity with at least one cell, each of the EEC sensors comprising: (1) a planar semiconductor layer, the semiconductor layer having a planar surface, (2) a metal shunt that contacts and partially covers the planar surface of the semiconductor layer, thereby defining a planar semiconductor/metal interface;
    perturbing the EEC sensors with an electric charge to thereby produce a voltage response by each of the perturbed EEC sensors;
    for each of the perturbed EEC sensors, measuring the produced voltage response; and
    generating an image from the voltage responses, wherein the generated image is indicative of at least one characteristic of the at least one cell.

12. The method of claim 11 wherein the EEC sensors comprise nanoscale EEC sensors, and wherein the generated image has a nanoscale spatial resolution.

13. The method of claim 12 wherein the at least one cell comprises at least one living cell, and wherein the perturbing step further comprises perturbing the nanoscale EEC sensors with an electric charge produced by the at least one living cell.

14. An apparatus comprising:
    a planar semiconductor layer, the semiconductor layer having a planar surface; and
    a metal shunt that contacts and partially covers the planar surface of the semiconductor layer, thereby defining a planar semiconductor/metal interface.

15. The apparatus of claim 14 wherein the semiconductor/metal interface is configured to exhibit a change in resistance thereof in response to a perturbation.

16. The apparatus of claim 15 wherein the semiconductor layer and the metal shunt are arranged as a nanoscale sensor, and wherein the sensor, in response to an application of a bias current, is configured to permit a tunneling of a portion of the bias current from the semiconductor layer through the semiconductor/metal interface to the metal shunt.

17. The apparatus of claim 16 wherein the sensor further comprises a plurality of leads that contact the semiconductor layer, the leads configured to provide the bias current to the semiconductor layer.

18. The apparatus of claim 17 wherein the leads do not contact the metal shunt.

19. The apparatus of claim 17 wherein the planar surface comprises a first planar surface, wherein the planar semiconductor layer further comprises a second planar surface opposite the first planar surface, and wherein sensor further comprises a substrate, wherein the substrate contacts the planar semiconductor layer along the second planar surface.

20. The apparatus of claim 19 wherein the semiconductor layer comprises GaAs, wherein the metal shunt comprises Au, and wherein the substrate comprises GaAs.

21. The apparatus of claim 17 wherein semiconductor layer comprises GaAs, and wherein the metal shunt comprises Au.

22. The apparatus of claim 17 wherein the leads comprise a plurality of current leads and a plurality of voltage leads, the current leads configured for applying the bias current, the voltage leads for measuring a voltage signal representative of the resistance change.

23. The apparatus of claim 22 wherein the voltage leads are asymmetrically spaced along a width of the semiconductor layer.

24. The apparatus of claim 22 wherein the current leads are asymmetrically spaced along a width of the semiconductor layer.

25. The apparatus of claim 14 wherein the planar semiconductor layer and the metal shunt exhibit a circular shape.

26. The apparatus of claim 14 wherein the semiconductor layer and the metal shunt are arranged as a nanoscale sensor.

27. The apparatus of claim 16 wherein the nanoscale sensor has a nanoscale length.

28. The apparatus of claim 16 wherein the nanoscale sensor has a nanoscale length and a nanoscale width.

29. The apparatus of claim 15 wherein the semiconductor/metal interface is configured as a Schottky barrier.

30. The apparatus of claim 29 wherein the Schottky barrier is configured to respond to the perturbation by reapportioning a flow of tunneling current as between the semiconductor layer and the metal shunt, thereby causing a measurable voltage response indicative of the perturbation.

31. The apparatus of claim 29 wherein the semiconductor layer and the metal shunt are arranged as a nanoscale sensor.

32. The apparatus of claim 31 further comprising a plurality of the nanoscale sensors formed into an array.

33. The apparatus of claim 32 further comprising receiver electronics for receiving a plurality of signals representative of the resistance changes, the receiver electronics configured to generate image data based on the received signals.

34. The apparatus of claim 33 wherein the plurality of the nanoscale sensors correspond to a plurality of pixels such that the generated image data exhibits a nanoscale resolution.

35. The apparatus of claim 34 wherein each pixel comprises at least one of the nanoscale sensors.

36. The apparatus of claim 35 wherein a plurality of the pixels comprise a plurality of the nanoscale a sensors.

37. The apparatus of claim 36 wherein at least a plurality of the pixels that comprise a plurality of the nanoscale a sensors comprise a plurality of nanoscale sensors of different types.

38. The apparatus of claim 36 wherein at least a plurality of the pixels that comprise a plurality of the nanoscale sensors comprise a plurality of nanoscale sensors of a same type.

39. The apparatus of claim 35 wherein a plurality of the pixels are arranged as a plurality of composite pixels.

40. The apparatus of claim 39 wherein at least one of the composite pixels comprises a plurality of nanoscale a sensors of a same type arranged in a substantially straight line on the array.

41. The apparatus of claim 40 wherein the at least one composite pixel comprises at least one first composite pixel, and wherein at least one second composite pixel comprises a plurality of nanoscale sensors of a same type arranged in a substantially straight line on the array that is orthogonal to the straight line of the at least one first composite pixel.

42. The apparatus of claim 33 wherein the perturbation comprises an electric field perturbation.

43. The apparatus of claim 42 wherein the perturbation comprises a plurality of different types of perturbations.

44. The apparatus of claim 32 wherein the array further comprises a plurality of additional nanoscale sensors, each of the additional nanoscale sensors comprising:
   a planar semiconductor layer, the semiconductor layer of the additional nanoscale sensor having a planar surface;
   a metal shunt adjacent the semiconductor layer of the additional nanoscale sensor, thereby defining a semiconductor/metal interface that is perpendicular to the planar surface of the semiconductor layer of the additional nanoscale sensor; and
   wherein the semiconductor/metal interface of the additional nanoscale sensor is configured to exhibit a change in resistance thereof in response to a perturbation.

45. The apparatus of claim 44 wherein at least one of the additional nanoscale sensors comprises a nanoscale EAC sensor.

46. The apparatus of claim 45 further comprising a acoustic perturbation source for perturbing the array with acoustic energy.

47. The apparatus of claim 46 wherein the acoustic perturbation source comprises at least one selected from the group consisting of a scanning acoustic microscope, an ultrasound emitter using synthetic aperture focusing (SAFT), a medical imager with phased array transducers, a single element focused or unfocused ultrasound transducer, a shock wave device, and a mid-to-high intensity focused ultrasound array.

48. The apparatus of claim 44 wherein at least one of the additional nanoscale sensors comprises a nanoscale EOC sensor.

49. The apparatus of claim 48 further comprising a cover disposed to block light from perturbing a portion of at least one selected from the group consisting of the semiconductor layer and the metal shunt.

50. The apparatus of claim 48 further comprising a light perturbation source for perturbing the array with light.

51. The apparatus of claim 50 wherein the light perturbation source comprises a laser-emitting device.

52. The apparatus of claim 48 further comprising an object in contact with the array, wherein the object comprises at least one living cell, and wherein a fluorescent or phosphorescent emission produced by the at least one living cell serves as the perturbation for producing the resistance change in the at least one nanoscale EOC sensor.

53. The apparatus of claim 44 wherein at least one of the additional nanoscale sensors comprises a nanoscale EMR sensor.

54. The apparatus of claim 44 wherein at least one of the additional nanoscale-sensors comprises a nanoscale piezoelectric sensor.

55. The apparatus of claim 32 wherein of the nanoscale sensors exhibit a nanoscale length.

56. The apparatus of claim 55 wherein the nanoscale sensors exhibit a nanoscale length and a nanoscale width.

57. The apparatus of claim 32 wherein the resistance change is indicative of at least one characteristic of an object in proximity with the array, and wherein the array further comprises a protein coating on at least a plurality of the nanoscale sensors for contacting the object.

58. The apparatus of claim 57 wherein the protein coating comprises: at least one selected from the group consisting of fibronectin, vitronectin, collagen, and a protein-mimetic.

59. The apparatus of claim 32 wherein the semiconductor/metal interface is substantially perpendicular to a direction of the perturbation.

60. The apparatus of claim 32 further comprising the object in contact with the array, wherein the object comprises at least one living cell, and wherein an electric charge produced by the at least one living cell serves as the perturbation for producing the resistance change in at least one of the nanoscale sensors.

61. The apparatus of claim 32 wherein each of the nanoscale sensors is individually addressable.

62. The apparatus of claim 32 wherein all of the array's nanoscale sensors are configured to be responsive to the same type of perturbation.

63. The apparatus of claim 62 wherein the perturbation type comprises an electric field perturbation.

64. The apparatus of claim 31 further comprising an object in contact with the nanoscale sensor, and wherein the resistance change is indicative of at least one characteristic of the object.

65. The apparatus of claim 15 wherein the perturbation comprises an electric field perturbation.

66. The apparatus of claim 65 wherein the perturbation comprises a plurality of different types of perturbations.

67. A method comprising:
perturbing a sensor with a perturbation, the sensor comprising: (1) a planar semiconductor layer, the semiconductor layer having a planar surface, and (2) a metal shunt that contacts and partially covers the planar surface of the semiconductor layer, thereby defining a planar semiconductor/metal interface; and
measuring a signal representative of a resistance change for the semiconductor/metal interface in response to the perturbing step.

68. The method of claim 67 wherein the semiconductor/metal interface is configured as a Schottky barrier.

69. The method of claim 68 further comprising the Schottky barrier responding to the perturbation by reapportioning a flow of tunneling current as between the semiconductor layer and the metal shunt, thereby causing a measurable voltage response indicative of the perturbation.

70. The method of claim 68 wherein the sensor comprises a nanoscale sensor.

71. The method of claim 70 wherein the sensor comprises a plurality of the nanoscale sensors formed into an array, and wherein the measuring step comprises measuring the signals produced by the nanoscale sensors that are representative of the resistance changes in response to the perturbing step.

72. The method of claim 71 further generating an image based on the measured signals.

73. The method of claim 72 wherein the measured signals are indicative of at least one characteristic of an object in proximity to the nanoscale sensors, and wherein the image is representative of the at least one characteristic of the object.

74. The method of claim 73 further comprising repeating the perturbing, measuring, and generating steps over time to generate a real-time sequence of images that are representative of at least one characteristic of the object.

75. The method of claim 72 wherein the plurality of the nanoscale sensors correspond to a plurality of pixels such that the generated image exhibits a nanoscale resolution.

76. The method of claim 72 wherein the image generating step comprises generating an image of a cell based on the measured signals.

77. The method of claim 72 wherein the perturbing step comprises perturbing the nanoscale sensors with an electric field perturbation.

78. The method of claim 77 wherein the perturbation comprises a plurality of different types of perturbations.

79. The method of claim 71 wherein the array further comprises a plurality of additional nanoscale sensors, each of the additional nanoscale sensors comprising:
a planar semiconductor layer, the semiconductor layer of the additional nanoscale sensor having a planar surface;
a metal shunt adjacent the semiconductor layer of the additional nanoscale sensor, thereby defining a semiconductor/metal interface that is perpendicular to the planar surface of the semiconductor layer of the additional nanoscale sensor; and
wherein the semiconductor/metal interface of the additional nanoscale sensor is configured to exhibit a change in resistance thereof in response to a perturbation.

80. The method of claim 79 wherein at least one of the additional nanoscale sensors comprises a nanoscale EAC sensor.

81. The method of claim 80 wherein the perturbing step comprises perturbing the interface of the at least one nanoscale EAC sensor with an acoustic wave.

82. The method of claim 81 wherein the perturbing step further comprises perturbing the interface of the at least one nanoscale EAC sensor with an acoustic wave from a piezoelectric transducer, wherein the acoustic wave comprises a broadband plane wave whose direction is substantially perpendicular to the interface of the at least one EAC sensor.

83. The method of claim 82 wherein the acoustic wave has a frequency in a range of approximately 1 GHz to approximately 5 GHz.

84. The method of claim 79 wherein at least one of the additional nanoscale sensors comprises a nanoscale EOC sensor.

85. The method of claim 84 wherein the perturbing step comprises perturbing an exposed surface of the nanoscale EOC sensor with a light perturbation from an external light source.

86. The method of claim 84 wherein the measured signals are indicative of at least one characteristic of an object in proximity to the nanoscale sensors, the object comprising at least one living cell, and wherein the perturbing step comprises perturbing an exposed surface of the nanoscale EOC sensor with a signal emitted by the at least one living cell itself.

87. The method of claim 86 wherein the perturbation comprises a fluorescent or phosphorescent emission from the at least one living cell.

88. The method of claim 79 wherein at least one of the additional nanoscale sensors comprises a nanoscale EMR sensor.

89. The method of claim 79 wherein at least one of the additional nanoscale sensors comprises a nanoscale piezoelectric element.

90. The method of claim 71 further comprising:
implanting an array into a body prior to the perturbing and measuring steps.

91. The method of claim 90 wherein the perturbing step causes the array to produce a plurality of voltage responses that are representative of the resistance changes for the nanoscale sensors, the method further comprising wirelessly communicating the voltage responses to a remote signal processing device.

92. The method of claim 90 wherein the perturbing step causes the array to produce a plurality of voltage responses that are representative of the resistance changes for the nanoscale sensors, the method further comprising storing the voltage responses in a memory local to the array for subsequent retrieval.

93. The method of claim 90 wherein the implanting step comprises implanting the array into a patient's vasculature.

94. The method of claim 71 wherein the measured signals are indicative of at least one characteristic of an object in proximity to the nanoscale sensors.

95. The method of claim 94 wherein the object comprises at least one cell in vitro.

96. The method of claim 94 wherein the object comprises at least one living cell.

97. The method of claim 96 wherein the perturbing step comprises perturbing the sensor with a signal emitted by the at least one living cell itself.

98. The method of claim 97 wherein the perturbation comprises an electric charge produced by the at least one living cell.

99. The method of claim 96 further comprising coating the array with a protein to which the at least one living cell will adhere, the protein comprising fibronectin, vitronectin, collagen, and a protein-mimetic.

100. The method of claim 94 further comprising:
placing the object in contact with the array.

101. The method of claim 71 wherein the perturbing step further comprises perturbing the array with a plurality of different types of perturbations while an object is in proximity to the array, and wherein the measured signals are indicative of a plurality of different characteristics of the object.

102. The method of claim 101 wherein the perturbing step comprises perturbing the array with an acoustic wave and an electric field.

103. The method of claim 102 wherein the object comprises at least one living cell, and wherein the electric field comprises an electric field produced by the at least one living cell itself.

104. The method of claim 102 wherein the perturbing step comprises simultaneously perturbing the array with the acoustic wave and the electric field.

105. The method of claim 101 wherein the perturbing step comprises perturbing the array with light and electric field.

106. The method of claim 105 wherein the object comprises at least one living cell, and wherein the light comprises a fluorescent or phosphorescent emission from the at least one living cell itself.

107. The method of claim 105 wherein the object comprises at least one living cell, and wherein the electric field comprises an electric field.

108. The method of claim 105 wherein the perturbing step comprises simultaneously perturbing the array with the light and the electric field.

109. The method of claim 67 wherein the perturbing step comprises perturbing the sensor with an electric field perturbation.

110. The method of claim 109 wherein the perturbation comprises a plurality of different types of perturbations.

111. The method of claim 67 wherein the sensor comprises a nanoscale sensor, the method further comprising applying a bias current to the sensor, a portion of the bias current tunneling from the semiconductor layer through the semiconductor/metal interface to the metal shunt.

112. The method of claim 111 wherein the sensor further comprises a plurality of leads contacting the semiconductor layer, and wherein the applying step comprises applying the bias current to the semiconductor layer via the leads.

113. The method of claim 112 wherein the leads do not contact the metal shunt.

114. The method of claim 112 wherein the planar surface comprises a first planar surface, wherein the planar semiconductor layer further comprises a second planar surface opposite the first planar surface, and wherein sensor further comprises a substrate, wherein the substrate contacts the planar semiconductor layer along the second planar surface.

115. The method of claim 112 wherein semiconductor layer comprises GaAs, and wherein the metal shunt comprises Au.

116. The method of claim 112 wherein the leads comprise a plurality of current leads and a plurality of voltage leads, the current leads for applying the bias current, the voltage leads for measuring the signal.

117. The method of claim 116 wherein the voltage leads that are asymmetrically positioned along a width of the semiconductor layer.

118. The method of claim 116 wherein the current leads that are asymmetrically positioned along a width of the semiconductor layer.

119. The method of claim 67 wherein the planar semiconductor layer and the metal shunt exhibit a circular shape.

* * * * *